(12) United States Patent
Burnett et al.

(10) Patent No.: US 7,642,790 B2
(45) Date of Patent: *Jan. 5, 2010

(54) SYSTEMS AND METHODS FOR TESTING CONDUCTIVE MEMBERS EMPLOYING ELECTROMAGNETIC BACK SCATTERING

(75) Inventors: Gale D. Burnett, Ferndale, WA (US); Charles A. Frost, Albuquerque, NM (US)

(73) Assignee: Profile Technologies, Inc., Manhasset, NY (US)

( * ) Notice: Subject to any disclaimer, the term of this patent is extended or adjusted under 35 U.S.C. 154(b) by 243 days.

This patent is subject to a terminal disclaimer.

(21) Appl. No.: 11/729,366

(22) Filed: Mar. 27, 2007

(65) Prior Publication Data

US 2008/0191706 A1     Aug. 14, 2008

Related U.S. Application Data

(63) Continuation-in-part of application No. 11/287,183, filed on Nov. 25, 2005, now Pat. No. 7,196,529, which is a continuation-in-part of application No. 10/840,488, filed on May 6, 2004, now abandoned.

(60) Provisional application No. 60/468,626, filed on May 6, 2003.

(51) Int. Cl.
    *G01R 31/11* (2006.01)
(52) U.S. Cl. .................... 324/533; 324/700
(58) Field of Classification Search ........... 324/533, 324/700, 639, 642
    See application file for complete search history.

(56) References Cited

U.S. PATENT DOCUMENTS

| 1,745,419 A | 2/1930 | Henneberger |
| 2,113,749 A | 4/1938 | Statham |
| 2,124,579 A | 7/1938 | Knerr et al. |
| 2,522,362 A | 6/1950 | Gilbert |
| 2,570,912 A | 10/1951 | Bishop |
| 2,602,834 A | 7/1952 | Leslie et al. |
| 2,650,344 A | 8/1953 | Lloyd |
| 2,725,526 A | 11/1955 | Strincifield et al. |
| 2,731,598 A | 1/1956 | Herbert |
| 2,887,652 A | 5/1959 | Bendayan |

(Continued)

FOREIGN PATENT DOCUMENTS

DE         2210167        9/1973

(Continued)

*Primary Examiner*—Vincent Q Nguyen
(74) *Attorney, Agent, or Firm*—Michael R. Schacht; Schacht Law Office, Inc.

(57) ABSTRACT

A system or method of analyzing a conductive member for the presence an anomaly. A conductive pipe member is analyzed for the presence an anomaly the electromagnetic properties of which are non-linear. The electromagnetic properties of the pipe member at the anomaly are altered by applying a direct current perturbation signal to the pipe member. At least one test source signal is applied to a first test location on the pipe member remote from the anomaly to cause the at least one test source signal to travel along the pipe through the anomaly. At least one test return signal associated with the at least one test source signal traveling through the anomaly is detected. The at least one test return signal is analyzed for characteristics associated with the anomaly.

34 Claims, 24 Drawing Sheets

U.S. PATENT DOCUMENTS

| | | |
|---|---|---|
| 2,935,728 A | 5/1960 | Morgan |
| 3,055,209 A | 9/1962 | Reid et al. |
| 3,264,864 A | 8/1966 | Reid et al. |
| 3,273,055 A | 9/1966 | Quittner |
| 3,400,363 A | 9/1968 | Silverman |
| 3,526,831 A | 9/1970 | Smith |
| 3,600,674 A | 8/1971 | Roberts |
| 3,609,533 A | 9/1971 | Pardis |
| 3,670,240 A | 6/1972 | Maranchak et al. |
| 3,747,085 A | 7/1973 | Bala et al. |
| 3,757,287 A | 9/1973 | Bealor, Jr. |
| 3,909,712 A | 9/1975 | Rietz et al. |
| 3,924,179 A | 12/1975 | Dozier |
| 3,991,364 A | 11/1976 | Wiznerowicz |
| 3,992,923 A | 11/1976 | Roberts |
| 4,039,938 A | 8/1977 | Link |
| 4,063,161 A | 12/1977 | Pardis |
| 4,083,229 A | 4/1978 | Anway |
| 4,099,117 A | 7/1978 | Erath |
| 4,112,349 A | 9/1978 | Weber |
| 4,118,662 A | 10/1978 | Weber |
| 4,142,143 A | 2/1979 | Daniel |
| 4,172,382 A | 10/1979 | Murphy et al. |
| 4,178,576 A | 12/1979 | Schmidt, Jr. et al. |
| 4,255,710 A | 3/1981 | Weber |
| 4,289,019 A | 9/1981 | Claytor |
| 4,291,204 A | 9/1981 | Crick |
| 4,319,348 A | 3/1982 | Suzuki |
| 4,326,416 A | 4/1982 | Fredberg |
| 4,347,622 A | 8/1982 | Bernatowicz et al. |
| 4,389,593 A | 6/1983 | DeSantis et al. |
| 4,404,514 A | 9/1983 | Reichert, Jr. |
| 4,427,940 A | 1/1984 | Hirama et al. |
| 4,430,613 A | 2/1984 | French |
| 4,471,294 A | 9/1984 | Nielsen |
| 4,495,465 A | 1/1985 | Tomaiuolo et al. |
| 4,538,103 A | 8/1985 | Cappon |
| 4,591,785 A | 5/1986 | Hoehn, Jr. |
| 4,648,081 A | 3/1987 | Burns |
| 4,695,788 A | 9/1987 | Marshall |
| 4,739,276 A | 4/1988 | Graube |
| 4,742,298 A | 5/1988 | Ando et al. |
| 4,755,742 A | 7/1988 | Agoston et al. |
| 4,769,598 A | 9/1988 | Krieg et al. |
| 4,829,284 A | 5/1989 | Pfaff |
| 4,839,593 A | 6/1989 | Spies |
| 4,843,319 A | 6/1989 | Lara |
| 4,843,320 A | 6/1989 | Spies |
| 4,855,656 A | 8/1989 | Saitoh et al. |
| 4,906,925 A | 3/1990 | Kiminkinen |
| 4,906,937 A | 3/1990 | Wikstrom et al. |
| 4,911,012 A | 3/1990 | Ziska |
| 4,929,896 A | 5/1990 | Lara |
| 4,929,898 A | 5/1990 | Spies |
| 4,929,903 A | 5/1990 | Saigo et al. |
| 4,970,467 A | 11/1990 | Burnett |
| 4,982,198 A | 1/1991 | Shafai et al. |
| 4,990,851 A | 2/1991 | Spies |
| 4,996,879 A | 3/1991 | Kruka et al. |
| 5,070,537 A | 12/1991 | Ohira et al. |
| 5,087,873 A | 2/1992 | Murphy et al. |
| 5,121,058 A | 6/1992 | Allison et al. |
| 5,122,773 A | 6/1992 | Chahbazian |
| 5,126,654 A | 6/1992 | Murphy et al. |
| 5,189,374 A | 2/1993 | Burnett |
| 5,243,294 A | 9/1993 | Burnett |
| 5,254,944 A | 10/1993 | Holmes et al. |
| 5,270,661 A | 12/1993 | Burnett |
| 5,321,356 A | 6/1994 | Weischedel |
| 5,333,502 A | 8/1994 | Clark, Jr. et al. |
| 5,389,216 A | 2/1995 | Balkanli |
| 5,404,104 A | 4/1995 | Rivola et al. |
| 5,446,369 A | 8/1995 | Byrne et al. |
| 5,481,198 A | 1/1996 | Patel |
| 5,526,691 A | 6/1996 | Latimer et al. |
| 5,530,367 A | 6/1996 | Bottman |
| 5,581,037 A | 12/1996 | Kwun et al. |
| 5,635,645 A | 6/1997 | Ottes et al. |
| 5,644,244 A | 7/1997 | Marrelli et al. |
| 5,719,503 A | 2/1998 | Burnett |
| 5,793,293 A | 8/1998 | Melamud et al. |
| 5,828,219 A | 10/1998 | Hanlon et al. |
| 5,828,220 A | 10/1998 | Carney et al. |
| 5,854,557 A | 12/1998 | Tiefnig |
| 5,859,537 A | 1/1999 | Davis et al. |
| 5,864,229 A | 1/1999 | Lund |
| 5,905,194 A | 5/1999 | Strong |
| 6,051,977 A | 4/2000 | Masuda |
| 6,072,316 A | 6/2000 | Burnett |
| 6,137,449 A | 10/2000 | Kildal |
| 6,194,902 B1 | 2/2001 | Kuo et al. |
| 6,281,852 B1 | 8/2001 | Amarillas |
| 6,472,883 B1 * | 10/2002 | Burnett ..................... 324/534 |
| 6,646,451 B2 | 11/2003 | Lanan |
| 6,686,746 B2 | 2/2004 | Allan et al. |
| 6,727,695 B2 | 4/2004 | Krivoi et al. |
| 6,889,557 B2 | 5/2005 | Richardson et al. |
| 7,196,529 B2 | 3/2007 | Burnett et al. |
| 2003/0016028 A1 | 1/2003 | Bass |
| 2004/0199340 A1 * | 10/2004 | Kersey et al. ................. 702/50 |

FOREIGN PATENT DOCUMENTS

| | | | |
|---|---|---|---|
| DE | 30 16 223 | A1 | 11/1980 |
| DE | 3532372 | | 3/1987 |
| DE | 3533479 | | 3/1987 |
| JP | 61209349 | | 9/1986 |
| WO | WO 89/06805 | | 7/1989 |
| WO | WO 97/32219 | A | 9/1997 |
| WO | WO 98/55877 | A | 12/1998 |

* cited by examiner

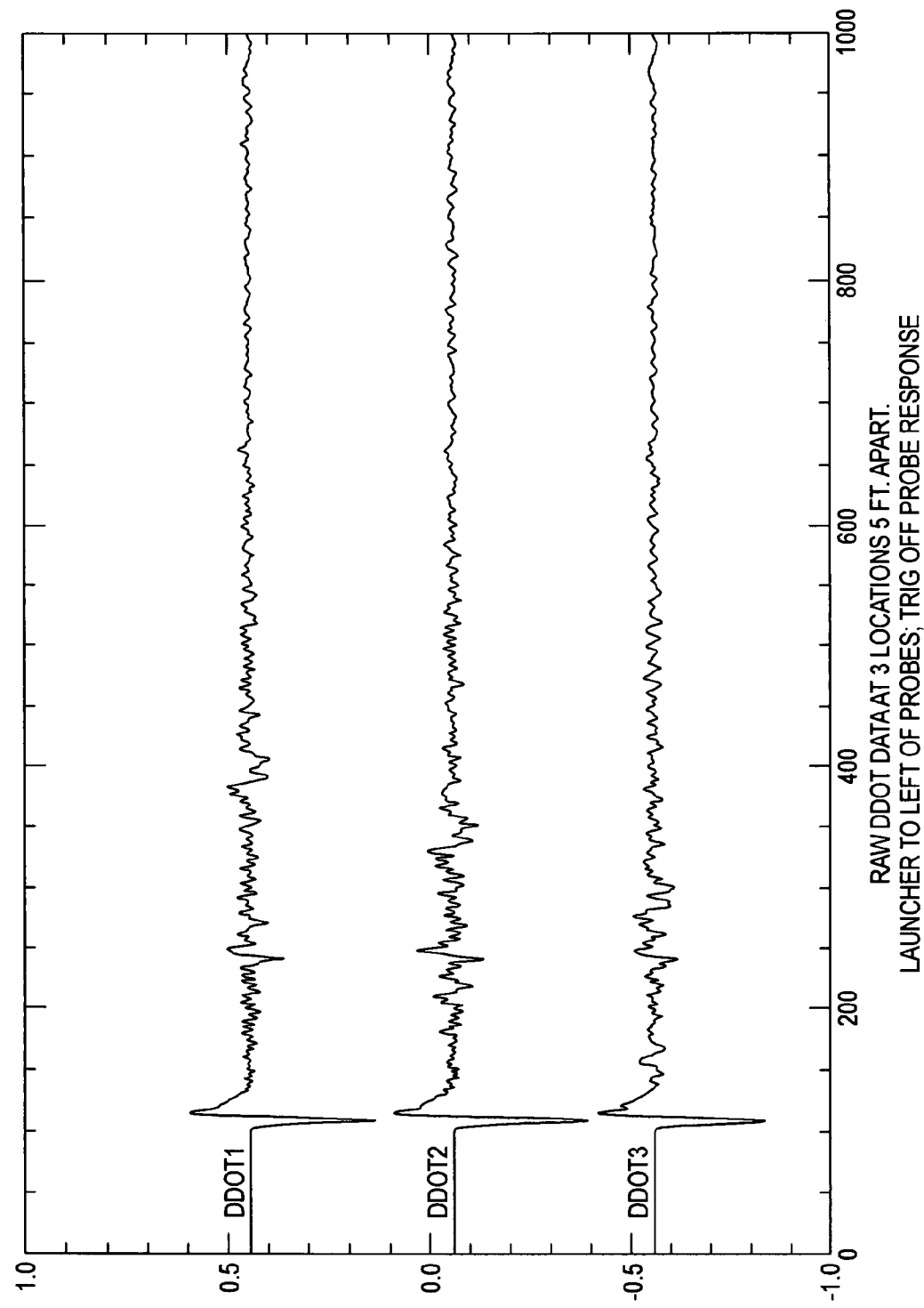

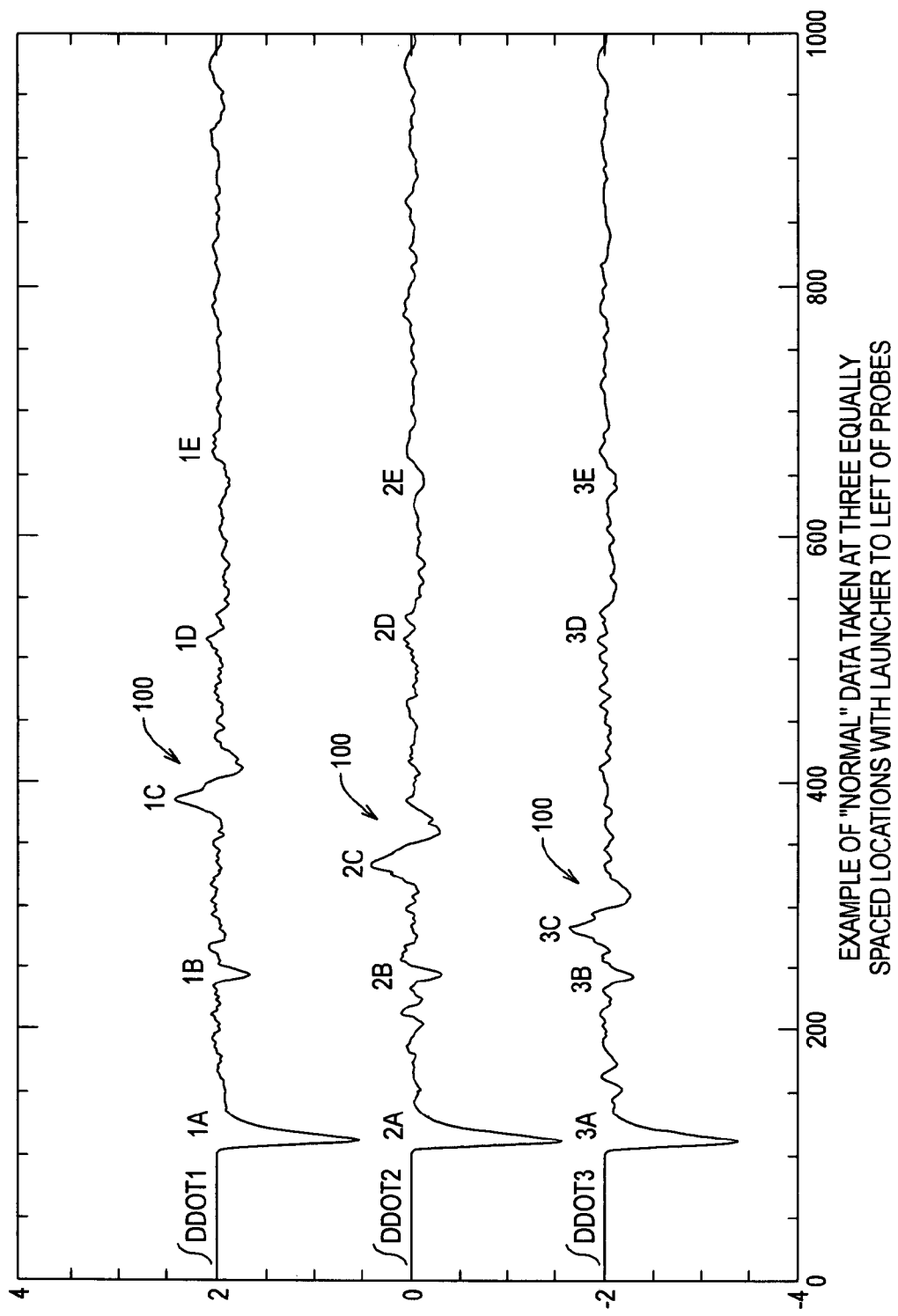

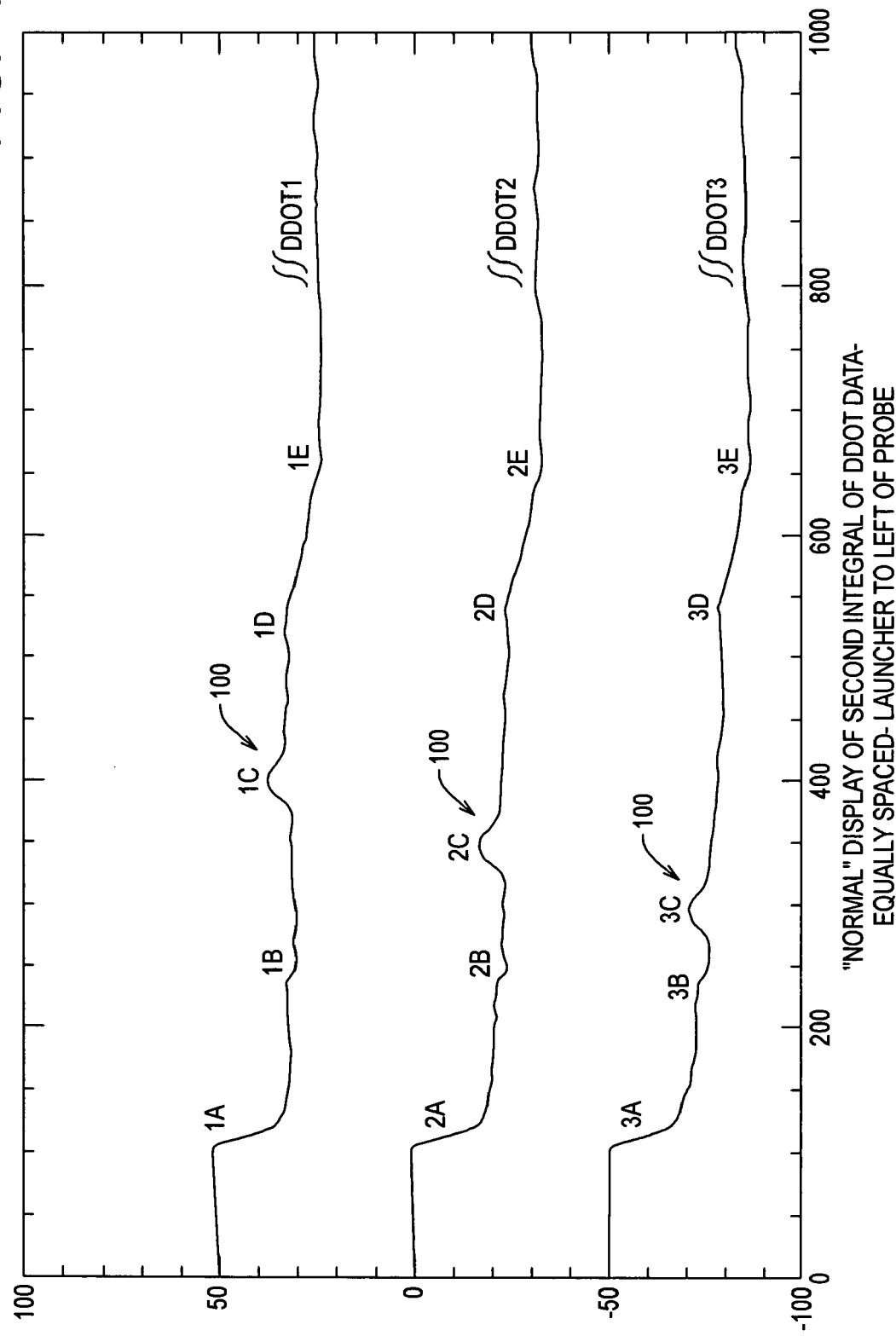

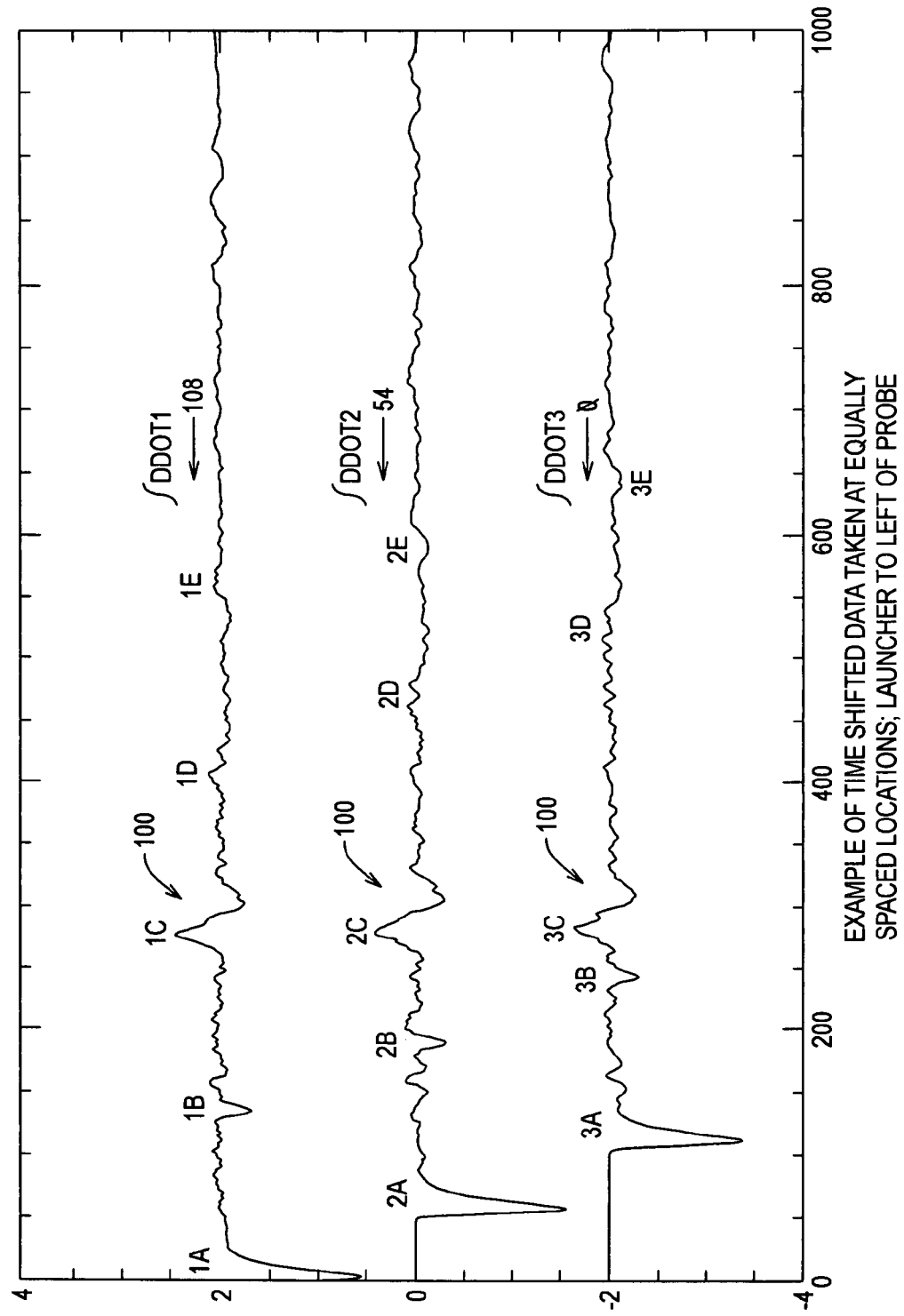

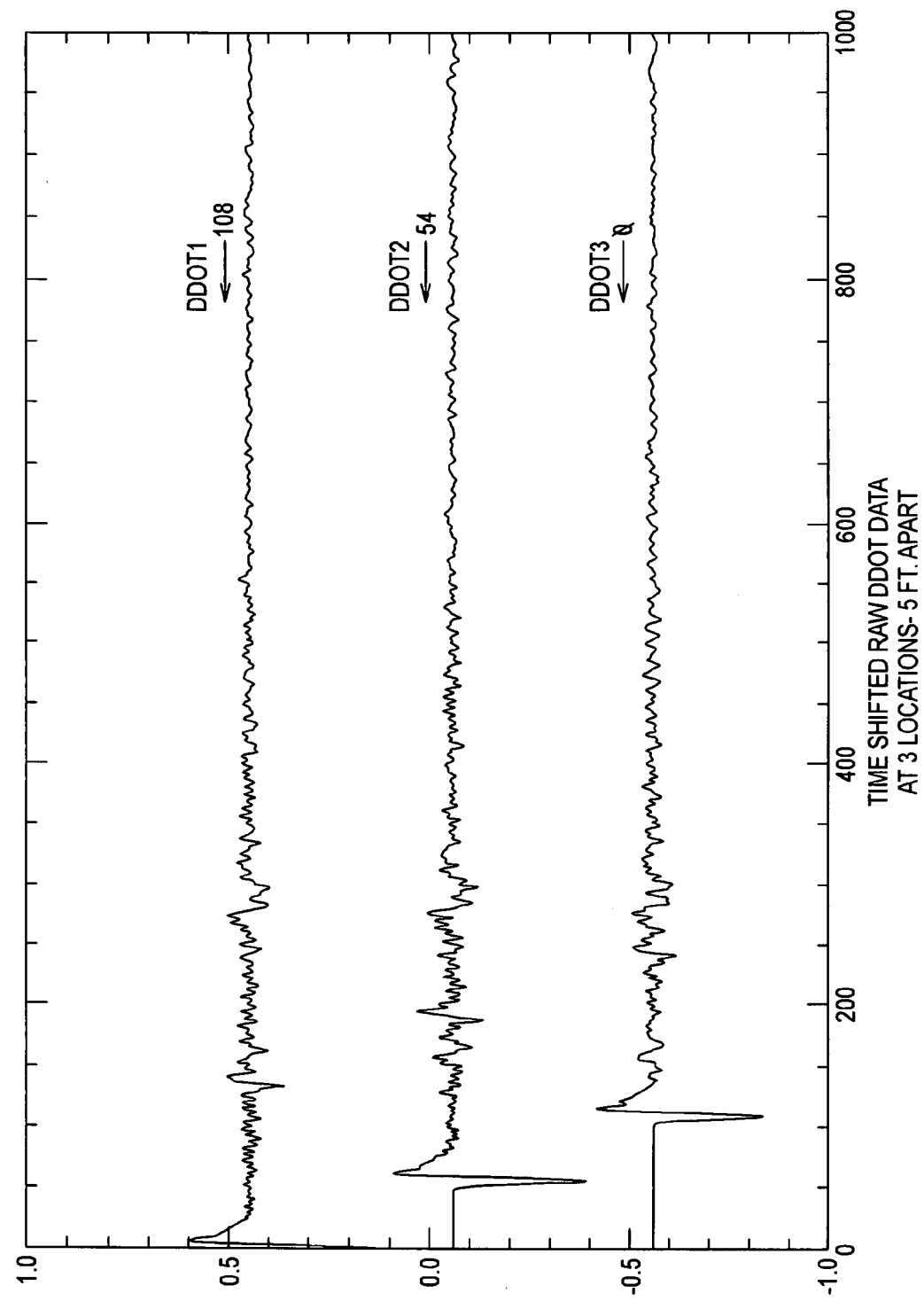

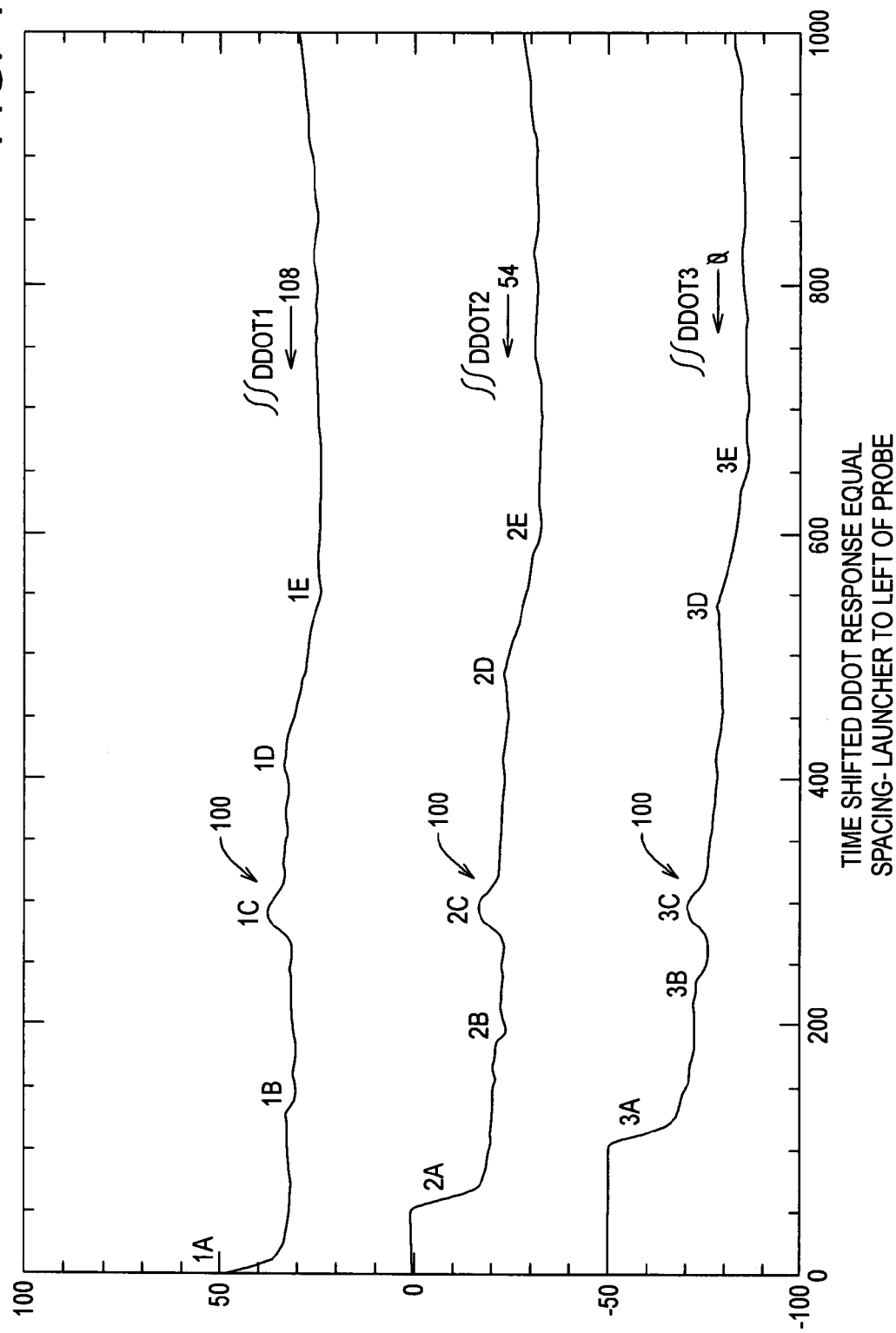

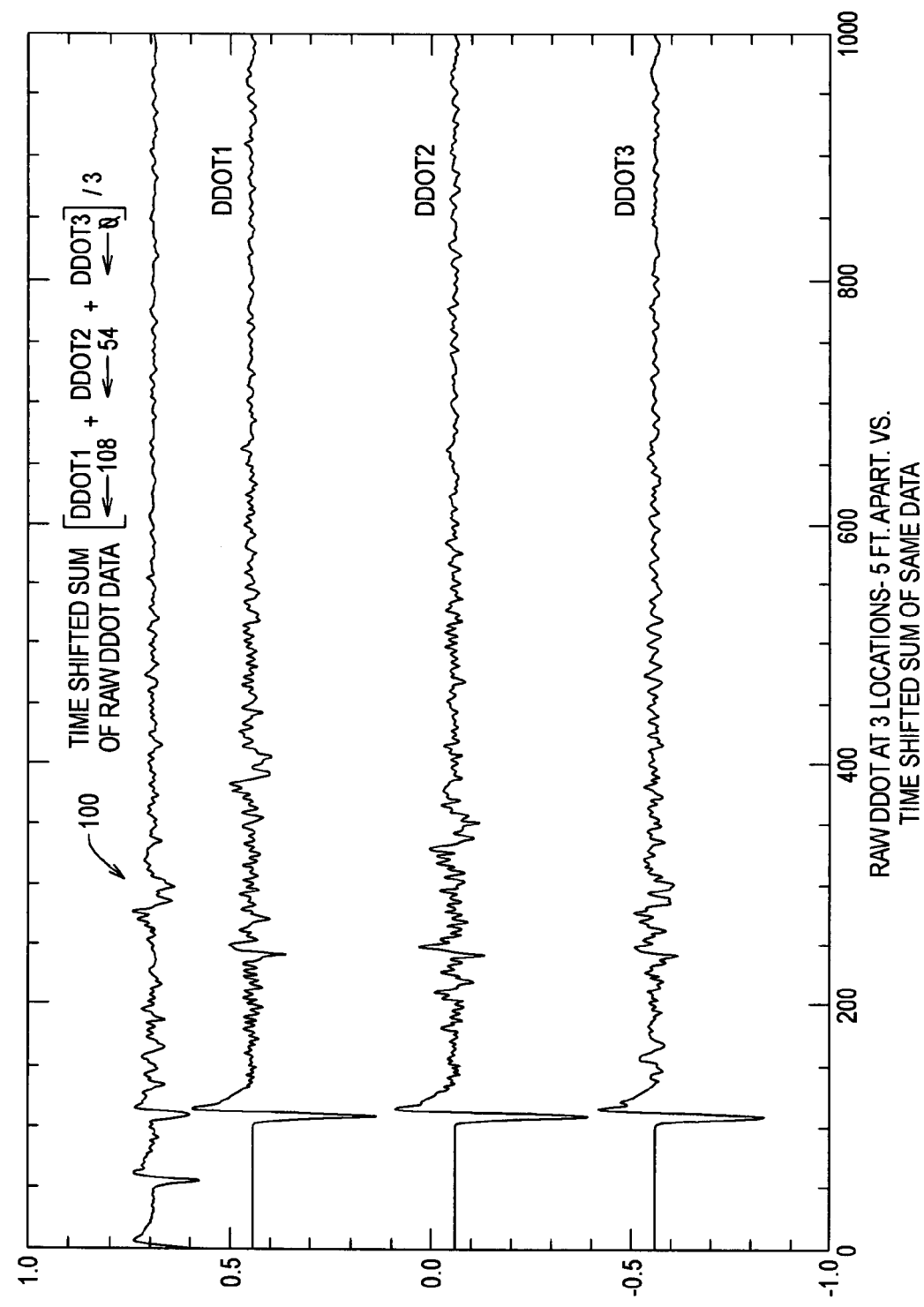

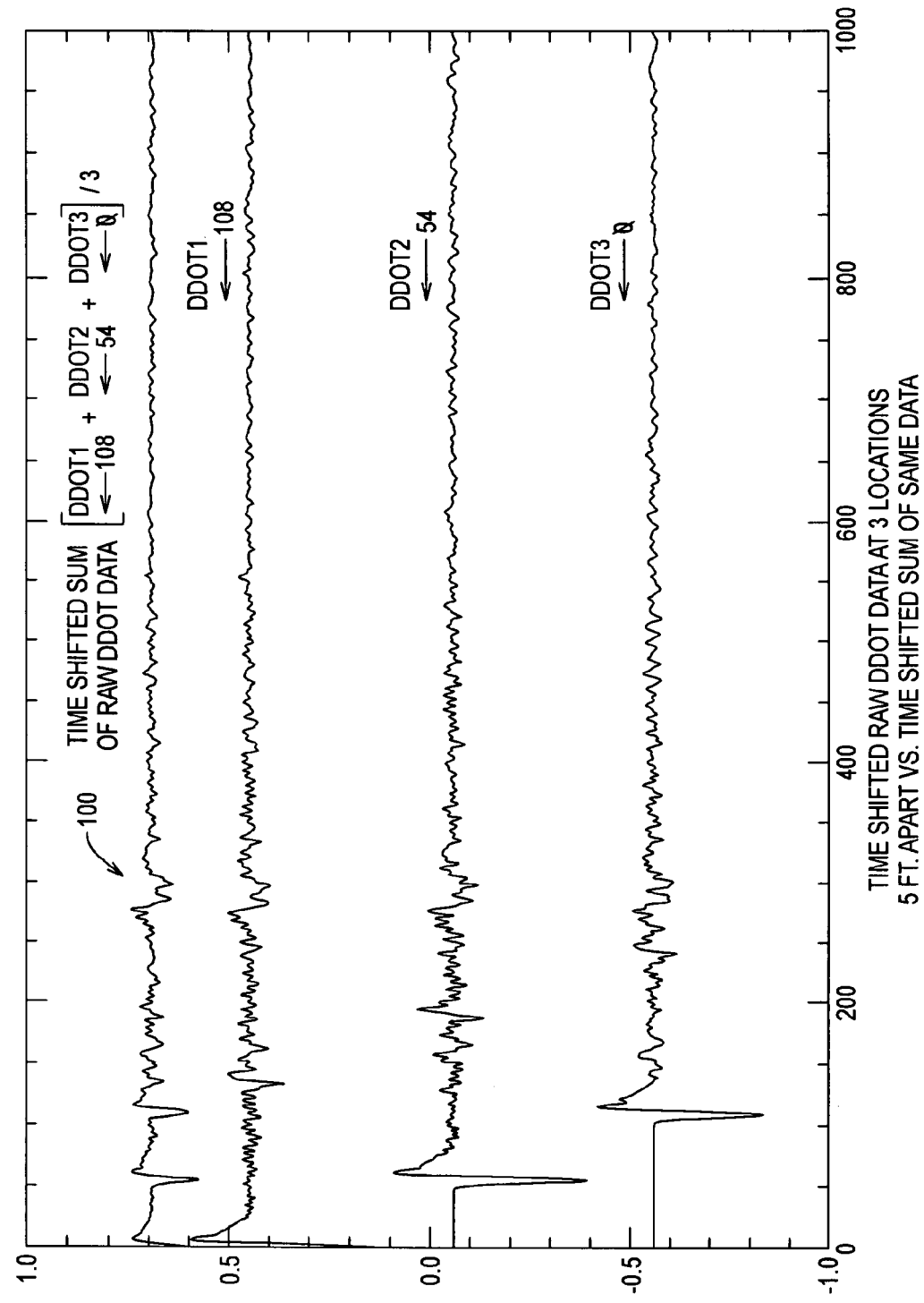

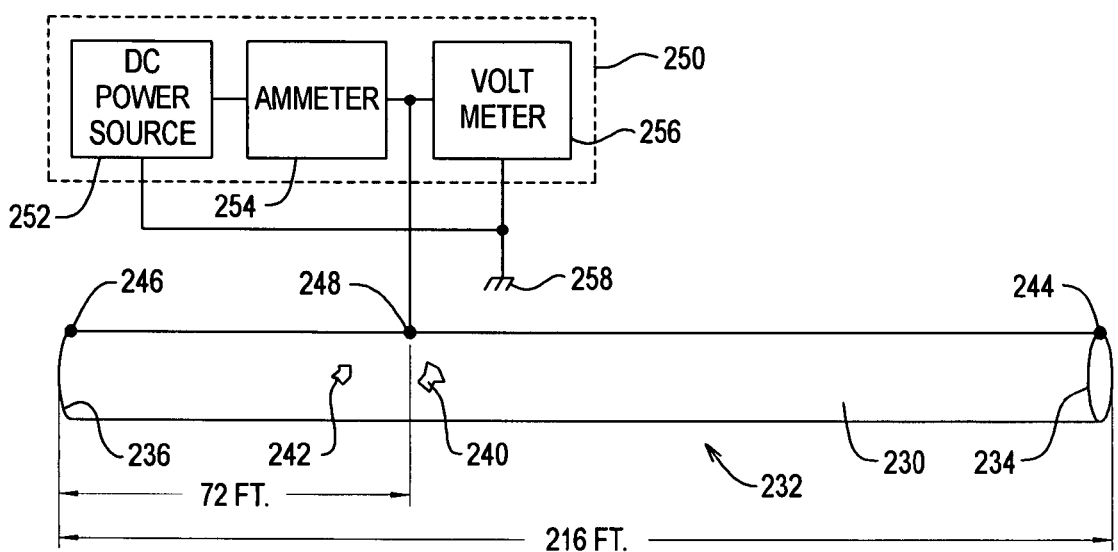

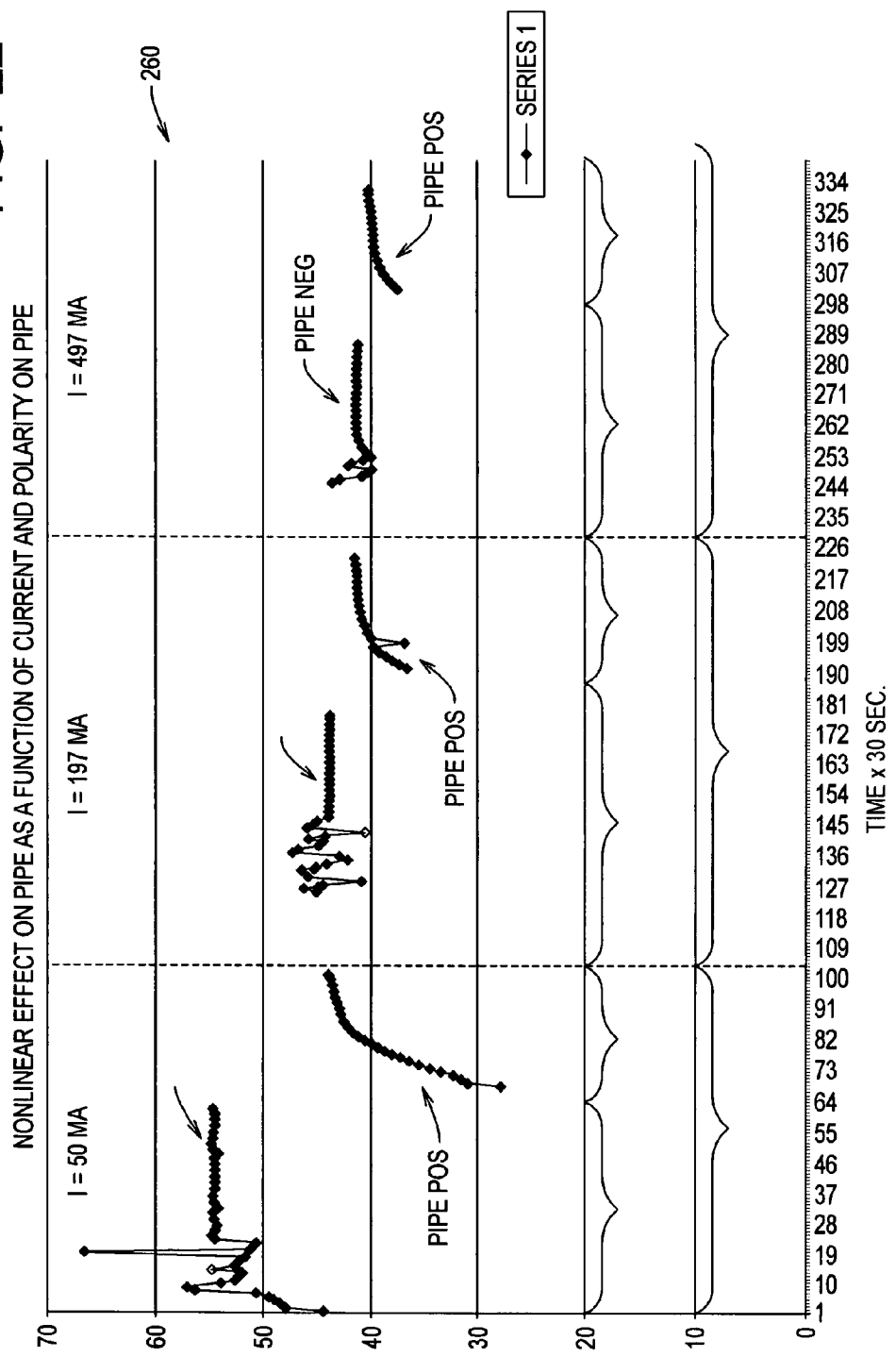

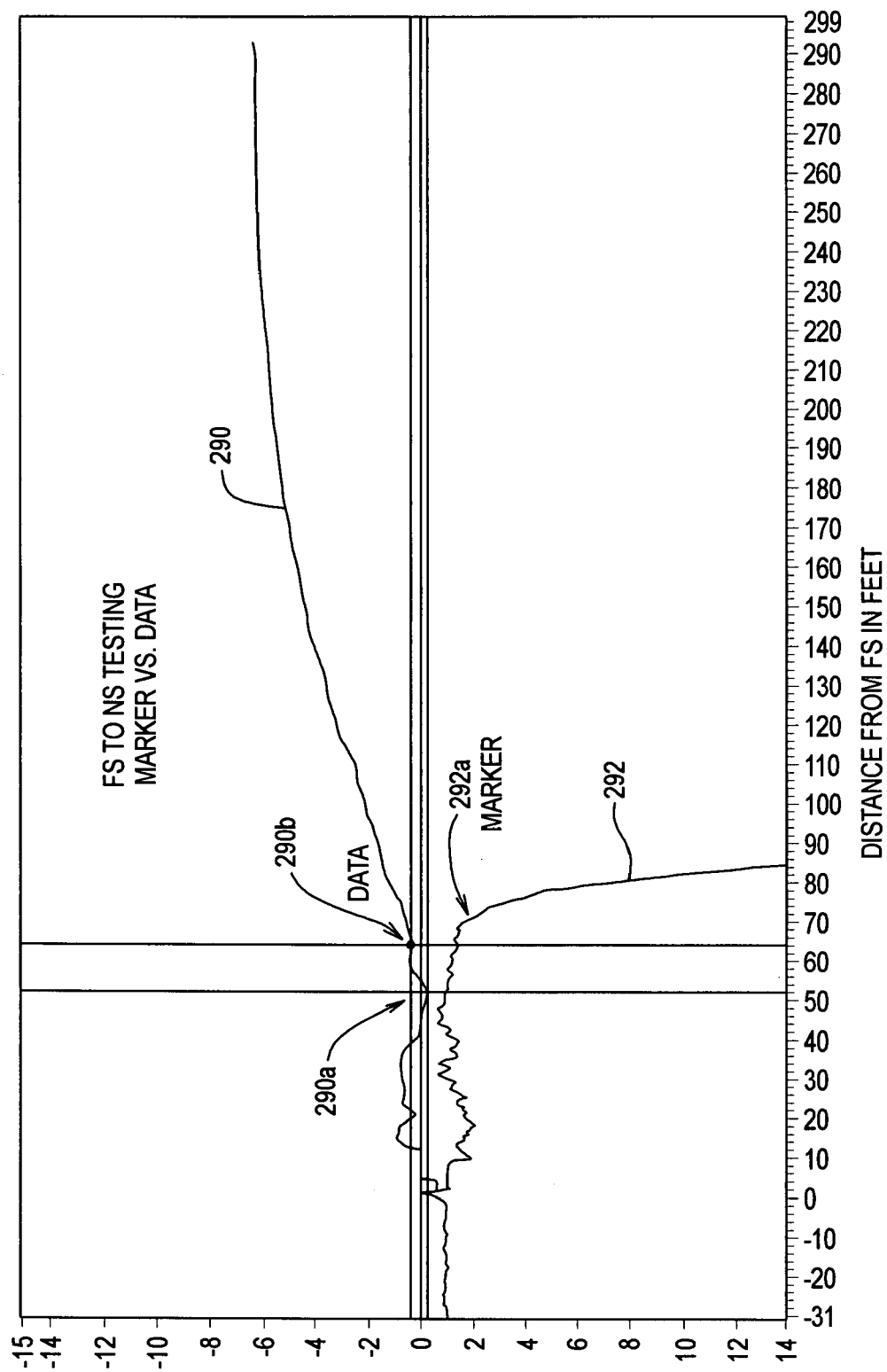

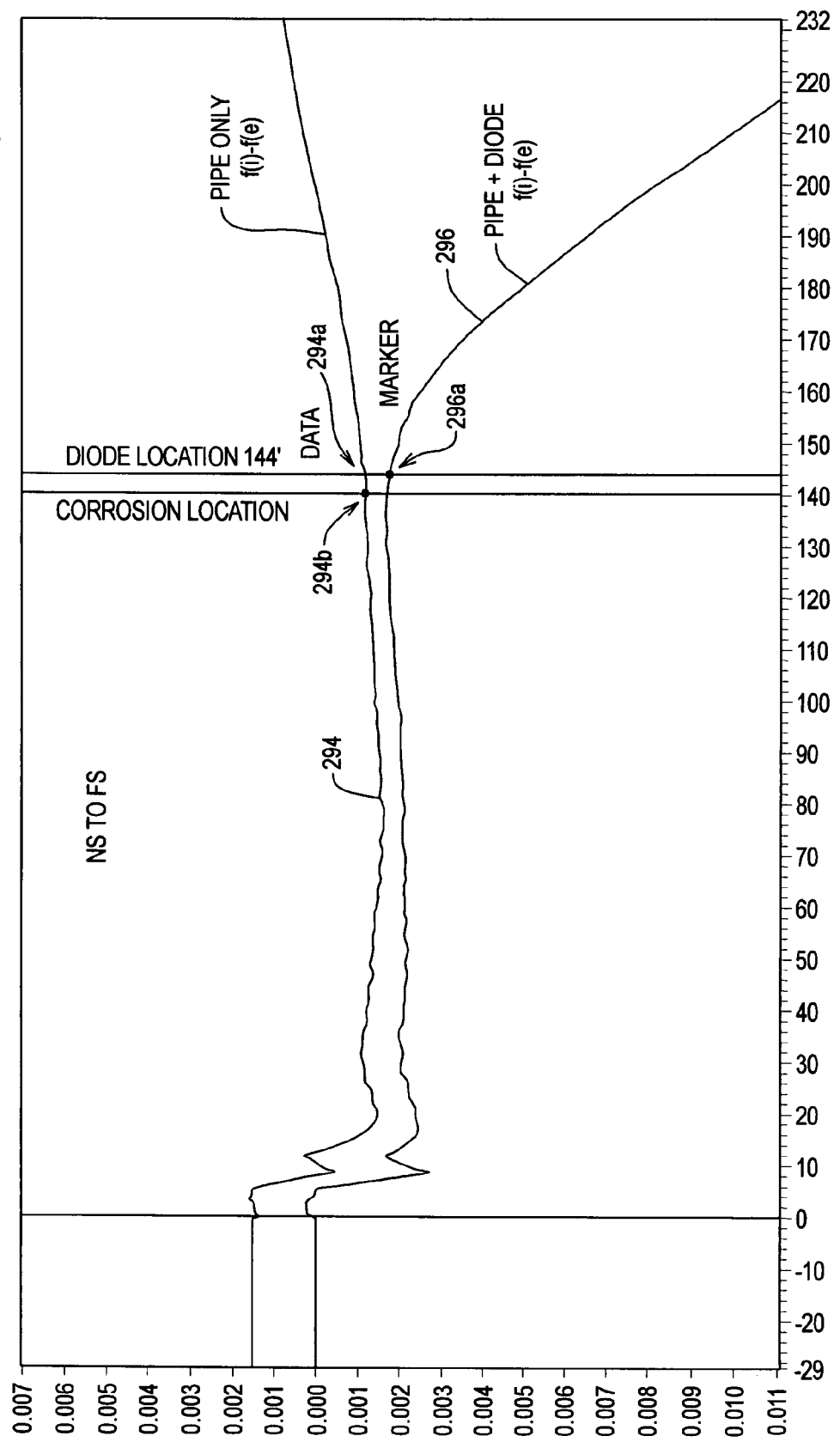

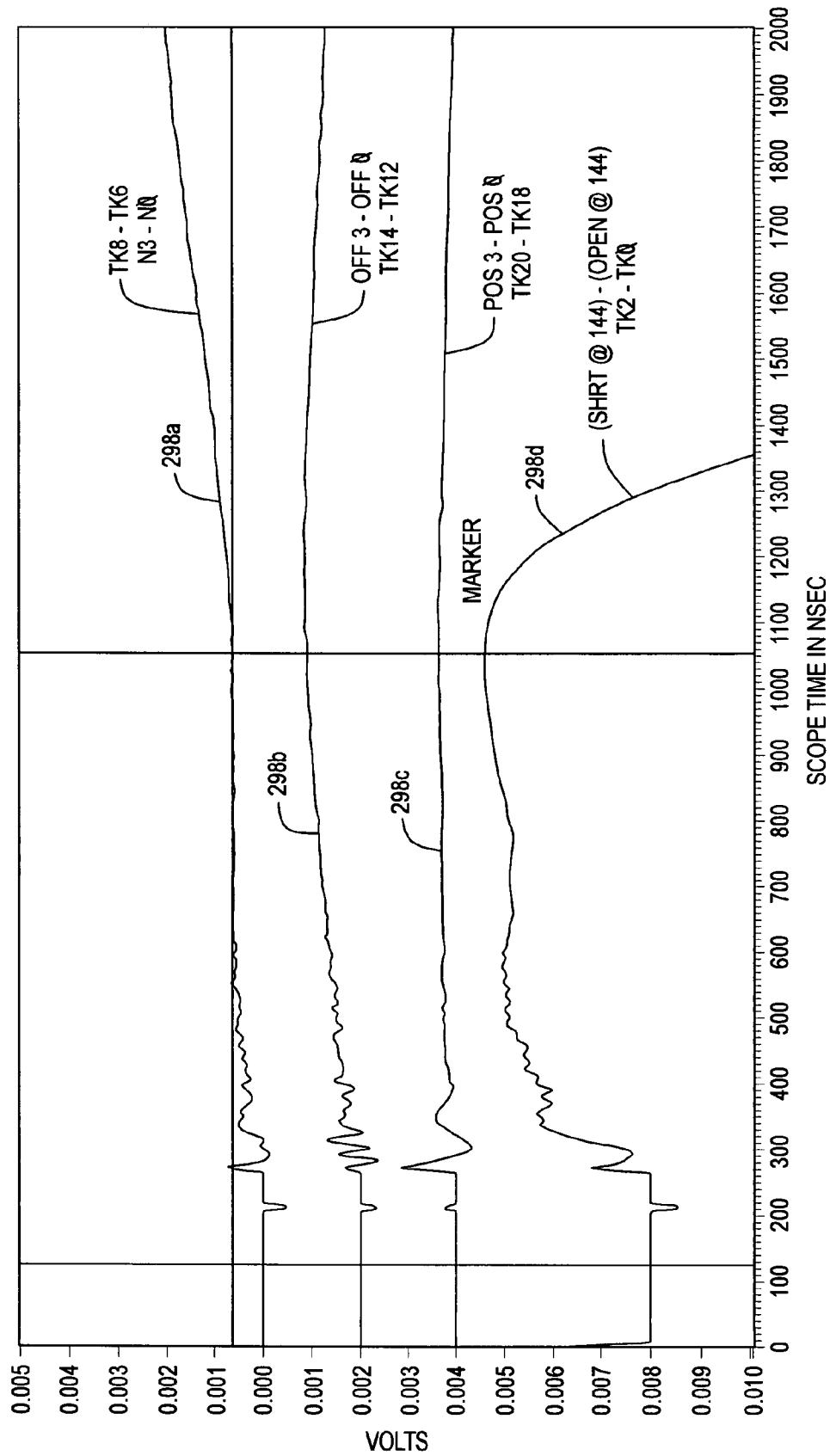

SYSTEMS AND METHODS FOR TESTING CONDUCTIVE MEMBERS EMPLOYING ELECTROMAGNETIC BACK SCATTERING

RELATED APPLICATIONS

This application is a continuation-in-part of U.S. patent application Ser. No. 11/287,183 filed Nov. 25, 2005 now U.S. Pat. No. 7,196,529, which is a continuation-in-part of U.S. patent application Ser. No. 10/840,488 filed May 6, 2004, now abandoned, which claims priority of U.S. Provisional Patent Application No. 60/468,626 filed May 6, 2003. The contents of all related applications listed above are incorporated herein by reference.

TECHNICAL FIELD

The present invention relates to testing systems and methods for conductive members and, more specifically, to systems and methods for detecting anomalies such as corrosion at remote locations on insulated, shielded metallic pipes.

BACKGROUND OF THE INVENTION

Corrosion of steel pipes can degrade the structural integrity of the pipeline system. In some pipeline systems, the metallic pipe is insulated with a urethane foam covering and protected by an outer metallic shield. In other pipeline systems, the metallic pipe is buried. For insulated, shielded pipes, visual inspection is impossible without physically removing the insulation and outer shield. For buried pipes, visual inspection is also impossible without excavating the pipe.

Current methods of testing pipe without removing the insulation and outer shield or excavation include acoustic wave propagation through the metal and x-ray radiography. However, acoustic wave propagation and x-ray radiography are only applicable to a single point location or over a short distance.

The need thus exists for improved systems and methods for testing for anomalies on a length of pipe without excavation or removing the shielding and insulation.

SUMMARY OF THE INVENTION

The present invention may be embodied as a system or method of analyzing a conductive member for the presence an anomaly. A conductive pipe member is analyzed for the presence an anomaly the electromagnetic properties of which are non-linear. The electromagnetic properties of the pipe member at the anomaly are altered by applying a direct current perturbation signal to the pipe member. At least one test source signal is applied to a first test location on the pipe member remote from the anomaly to cause the at least one test source signal to travel along the pipe through the anomaly. At least one test return signal associated with the at least one test source signal traveling through the anomaly is detected. The at least one test return signal is analyzed for characteristics associated with the anomaly.

BRIEF DESCRIPTION OF THE DRAWINGS

FIGS. 2-14 are graphs plotting data obtained using the systems described in FIGS. 1A, 1B, and 15.

FIG. 21 is a schematic block diagram depicting a test system that demonstrates that corroded pipe has measurable DC nonlinear resistance;

FIG. 22 is a plot of resistance in ohms versus time illustrating data collected using the test system depicted in FIG. 21;

FIG. 24 is plot of change of impedance versus distance obtained by measuring at a first end of the elongate conductive member analyzed by the system of FIG. 23B demonstrating the remote detection of corrosion nonlinearity activated using an external DC bias supply;

FIG. 25 is plot of change of impedance versus distance obtained by measuring at a second end of the elongate conductive member analyzed by the system of FIG. 23C demonstrating the remote detection of corrosion nonlinearity activated using an external DC bias supply; and FIG. 26 is a plot four different traces of voltage versus time obtained using the system of FIG. 23 comparing three different bias conditions with a calibration marker.

DETAILED DESCRIPTION OF THE INVENTION

Figure 1A:
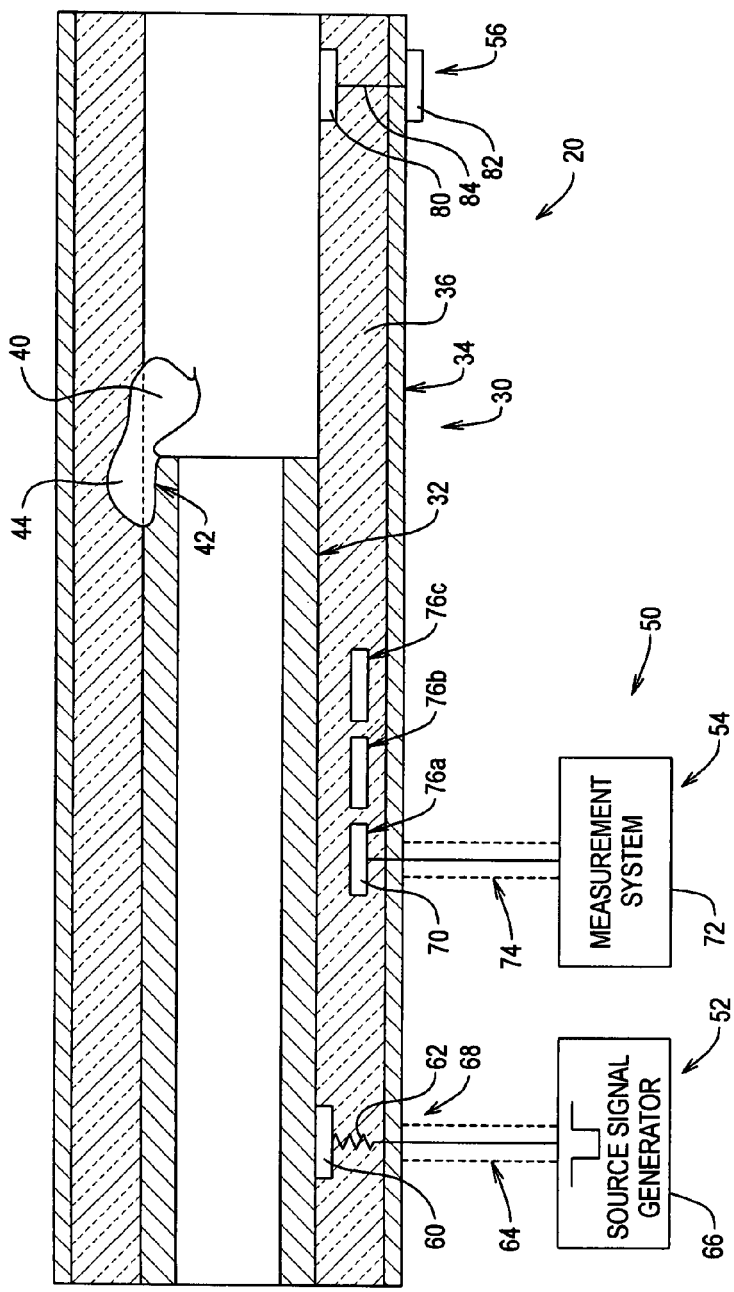
FIGS. 1A and 1B are somewhat schematic views of systems for testing for anomalies on a pipe system.

Referring initially to FIG. 1 of the drawing, depicted therein is an example measurement setup 20 constructed in accordance with, and embodying, the principles of the present invention. The example measurement system 20 is designed test for anomalies in a pipeline system 30 comprising a conductive pipe 32, a conductive outer shield 34, and insulation 36. The pipe 32 and outer shield 34 are typically metallic, and the insulation 36 is typically urethane foam. The pipe 32 is typically centered in the shield 34 by the insulating layer 36. The pipeline system 30 thus effectively forms a constant impedance coaxial transmission line capable of propagating electromagnetic waves in the transverse electromagnetic (TEM), Transverse Electric (TE), and Transverse Magnetic (TM) modes. The TEM waves are dominant, and the TE and TM waves re higher order propagating modes.

Illustrated at 40 in FIG. 1 is an anomaly such as an area of corrosion on the outside of the pipe 32. The anomaly 40 can affect the wave transmission by the pipeline system 30. In particular, the impedance of a coaxial transmission line is a function of the diameter of the inner and outer conductor and the dielectric and magnetic properties of the material between them.

In the context of the pipeline system 30, the anomaly 40 can change the physical properties of the pipe 32, which in turn can affect the impedance of the system 30. For example, if the anomaly 40 is corrosion, the corrosion may thin the wall of the pipe 32 as shown at 42 in FIG. 1, thereby changing the impedance of the system 30. Corrosion can also spread into the insulating layer 36 as shown at 44 in FIG. 1, which can also affect the impedance of the pipeline system 30 by modifying the dielectric constant between pipe 32 and the shield 36. These changes in impedance can cause electromagnetic pulses propagating along the coaxial transmission line formed by the pipeline system 30 to reflect back toward the source of the electromagnetic wave or pulse.

FIG. 1 further illustrates an example test system 50 for detecting anomalies such as the anomaly 40 along the pipeline system 30. The example test system 50 comprises a source system 52, a sensor system 54, and a marker system 56. The source system 52 applies an electromagnetic pulse signal to the pipeline system 30. The sensor system 54 detects electromagnetic waves propagating along the pipeline system 30. The marker system 56 allows the test system 50 to be calibrated for a particular pipeline system 30 under test.

The example test system 50 tests the quality and integrity of metallic pipelines using the backward reflection of an electromagnetic impulse wave propagating along the pipe. In particular, the test system 50 propagates an electromagnetic impulse along the pipe and observes reflections from corrosion and other features which might affect the integrity of the system. The test system 50 thus allows improved electromagnetic inspection without removal of the entire shield and/or insulation. The test system 50 further allows testing of complete segments of pipe over extended lengths. Given the foregoing general understanding of the present invention, the example test system 20 will now be described in further detail.

The example source system 52 comprises a launcher 60, a matching resistor 62, a coaxial cable 64, and a pulse generator 66. The launcher 60 is used to excite waves which propagate in both directions along the pipe 32. In particular, the example launcher 60 makes electrical ohmic contact with the pipe 32 to cause waves to propagate in the insulation 36 between the pipe 32 and the outer shield 34. Exhibit A attached to Provisional Application Ser. No. 60/468,626 depicts details of one exemplary embodiment of the example launcher 60 described herein.

The matching resistor 62 is used to prevent reflected energy from traveling back toward the source system 52 through the coaxial data cable 64. The value of the matching resistor 62 is chosen to terminate the coaxial cable 64 in its characteristic impedance.

The pulse generator 66 forms the source of electromagnetic energy which excites the electromagnetic waves in the pipe system 30. The pulse generator 66 generates electromagnetic energy in any one of a number forms. As examples, the pulse generator 66 could provide a 500 Volt negative impulse with a duration of 2 nanoseconds or a step waveform with similar characteristics.

The coaxial cable 64 transmits the voltage pulses generated by the pulse generator 66 to an injection point 68 on the pipe 32 and shield 34. The application of the voltage pulses to the injection point 68 causes a current pulse to be launched in both directions from the injection point 68. The electromagnetic impulse propagates away from the injection point 68 in both directions in the space between the pipe 32 and the shield 34.

The sensor system 54 detects reflections from the anomaly 40 or other anomalies on the pipe system 30. The sensor system 54 comprises an electric field sensor 70, a measurement device 72, and a coaxial line 74. The electric field sensor 70 is a differentiating electric field sensor that detects electromagnetic waves by capacitive coupling of the electric field. One example of the electric field sensor 70 is known in the art as a D-dot probe. When subjected to a local electric field at the measurement point, a D-dot probe responds with an output voltage which is proportional to the time rate of change of the local electric field at the measurement point. The example D-dot probe used as the electric field sensor 70 consists of a small capacitive element which couples to the local electric field.

One example of an appropriate electric field sensor 70 is depicted in Exhibit B attached to Provisional Application Ser. No. 60/468,626. The output signal from the electric field sensor 70 is coupled to the measurement device 72 using the coaxial line 74. The measurement device 72 is preferably an oscilloscope or digital transient data recorder such as a Tektronix 3054 digital oscilloscope. The measurement device 72 records a signal which is proportional to the time derivative of the electric field at the location of the electric field sensor 70.

In use, the sensor system 54 will detect a first pulse as the exciting wave passes the electric field sensor 70. Later pulses are seen if signals reflect from variations in coaxial transmission line impedance, such as those caused by an anomaly 40 such as an area of corrosion on the pipe.

The signals recorded on the measurement device 72 can be numerically integrated to recover the local electric field waveform at the measurement point of the electric field sensor 70. Such a waveform will show an initial pulse coming from the source system 52, followed by reflections coming from anomalies on the line.

One object of the invention is to isolate reflections which come from the left or the right side of the injection point so that locations of anomalies can be identified unambiguously. Reflections will be seen from anomalies both to the right and to the left from the injection point. To separate these, the electric field sensor 70 may be moved to separate first, second, and/or third sensor locations 76a, 76b, and 76c which could, for example, be separated by a distance of 5 feet. Alternatively, three separate probes and/or measurement systems may be used, one for each of the sensor locations. Timing of the wave arrival of the incident and reflected pulse at the three separate locations 76a, 76b, and 76c allows both the distance and the direction of the anomaly to be determined by simple wave propagation calculation. Exhibit D attached to Provisional Application Ser. No. 60/468,626 illustrates and describes one example of the process of moving the sensor 70 to different sensor locations.

In addition, the three recorded signals from three separate locations can be time shifted by a fixed delay to bring each reflection from the right hand direction into time coincidence. Reflections from the left will not coincide. When added together the three time-shifted waveforms give a unidirectional measurement looking to the right. A second integration of the recorded data can give additional information about the magnitude and longitudinal extent of the measured anomalies.

The wave impedance of a coaxial transmission line is well known to depend on the spacing of the inner conductor and outer conductor and the dielectric and magnetic properties of the insulating media separating them. The Applicant has discovered that the wave impedance of the pipeline system 30 is similar to the wave impedance of a coaxial transmission line.

Referring initially to conductor spacing, a change in the conductor spacing causes a corresponding change in the impedance. In the context of the pipe system 30, if the effective diameter of the pipe 32 (the inner conductor) is increased, the conductor spacing decreases, yielding lower wave impedance and causing a reflection with polarity opposite to the source polarity. If the effective diameter of the pipe 32 decreases, the wave impedance is increased, causing a reflection with the same polarity as the source.

The insulating media between the inner and outer conductors also has an effect on wave impedance. In the context of the pipe system 30, if the dielectric constant of the insulating layer 36 is increased by the presence of moisture or higher density foam, the local wave impedance will be lowered, and a reflection with polarity opposite to the source will be generated.

The presence of corrosion products or other material with high dielectric constant in the space between the pipe and the outer shield will also cause a reflection with polarity opposite to the source impulse waveform. Conversely, a gap in the shield or a region of missing insulation will result in higher wave impedance, and this higher wave impedance will reflect a signal with the same polarity as the source. In addition, the duration of the reflected signal corresponds with the length over which the increased dielectric material occurs.

Using the test system 50, all of these factors can be used to determine the presence, extent, and location of anomalies along the pipe system 30.

The marker system 56 is used to calibrate or set a reference for the test system 50. The marker system comprises a pipe engaging member 80, a shield engaging member 82, and a shorting conductor 84. One example of a marker system 50 is shown in Exhibit C attached to Provisional Application Ser. No. 60/468,626.

The marker system 56 is placed at a known point on the pipe 32. The marker system 56 forms a direct short circuit connection between the pipe 32 and the shield 34. The exemplary pipe engaging member 80 and shield engaging member 82 magnetically attach to the pipe 32 and shield member 34, respectively. The shorting conductor 84 is typically a low inductance braid or strap conductor that connects the pipe engaging member 80 to the shield engaging member 82.

The marker system 56 provides a high quality connection between the pipe 32 and shield 34 which will reflect a known quantity of energy back toward the source system 52. The marker is used to calibrate the system 50 by determining a propagation speed of propagation in the particular insulation used as the insulating layer 36. Knowledge of wave propagation speed is used for range calibration. A wave speed of 1.07 nanoseconds per foot is typically measured for the urethane foam insulation used on the Alaska pipeline.

The marker system 56 also allows verification of proper operation of the system 50 by providing a known reflection signal. The level of attenuation of the reflected pulse from the marker system 46 gives an overall indication of the quality of the insulation forming the insulating layer 36 and also can reveal defects in the outer shield 34.

Referring now to FIGS. 2-14, depicted therein are graphs showing data collection and analysis using the principles of the present invention. The Ddot antenna, as it is used in this application, provides the derivative of the source field as it propagates and reflects in the space between the pipe and the shield. Therefore, the unaltered signal, propagating and reflecting along the pipe, will contain high frequency information which, often will hide or mask information concerning the physical condition of the pipe. FIG. 2 illustrates raw data collected using the Ddot antenna as described herein as the electric field sensor 70. Raw data as shown in FIG. 2 is beneficial in analyzing the pipeline system for very small flaws determined by a combination of pulse rise time, pulse width, and bandwidth of the detection hardware.

Integration of the raw data may more clearly illustrate the effect of the propagation path on the injected pulse. Since the Ddot antenna sensor differentiates the injected pulse, this integration approximately reproduces the injected pulse, smoothes out some of the very high frequency information in the raw data, and makes it easier to see larger anomalies that more closely correlate to pipeline anomalies that are of interest to the pipeline operating company. The chart depicted in FIG. 3 is an example of how the data appears after the first integration step.

To observe still another family of anomalies, one more level of integration may be used. The second integral of the raw Ddot data illustrates how the pipeline would respond to a step function, while using an impulse type pulse generator or pulser. The second integral of the data provides some additional smoothing, is less sensitive to small anomalies, and provides better visibility of larger anomalies. FIG. 4 illustrates how the data appears after the taking of the second integral of the raw data.

Figure 1B:
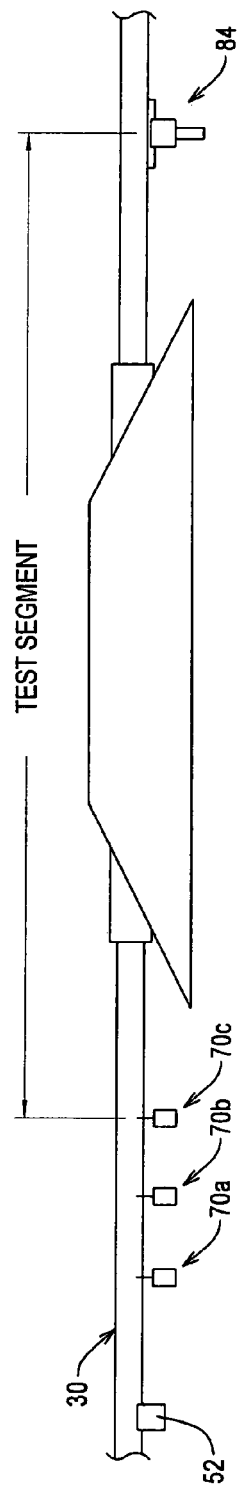

The data may also be time shifted to determine exactly what direction the anomalies come from and where they are located. FIG. 5 illustrates the time shifting of the data after the first integration step. FIG. 1B attached hereto is a somewhat schematic diagram illustrating a simplified layout of the particular pipeline configuration that was present where this data was acquired.

FIG. 5 illustrates five features identified using reference characters A, B, C, D, and E for each Ddot probe location. The first arrival of the pulse from the launcher is at position "A". Features "B", "D", and "E" in general are located to the left of the launcher, because they are not time shifted. Note however, that the feature at "C" is time shifted in the data as the Ddot probes are moved to the right. The anomalies to the right of the launcher will appear earlier in time as the Ddot is moved to the right. For this particular test, the pipe segment going under the roadway and through a casing lies to the right of the probes and is the segment of most interest.

FIG. 5 thus allows us to see the right side data properly oriented by time shifting probe positions #1 and #2 with respect to #3 as shown above. In this view, it is clear that the feature at "C" is in horizontal alignment at all three Ddot probe positions, the first arrival pulses at "A" and the features at "B", "D", and "E" are now not aligned. The differences are not quite as obvious because of all the high frequency in the raw data, but they can still be seen in close inspection of that data shown in FIG. 6.

FIG. 7 illustrates the time shifted double integral. FIG. 7 shows the normal double integral data. Note again that only location "C" is time shifted to the left, indicating that it is physically located to the right of the Ddot probes. When the data is time shifted with respect to Ddot location #3, all locations "C" are horizontally aligned, while "A", "B", "D", and "E" are no longer aligned.

One additional step can be taken to enhance the data. The time shifted data at each probe location may be summed and divided by the number of sensor locations 76, which in this case is equal to three.

Figure 10:
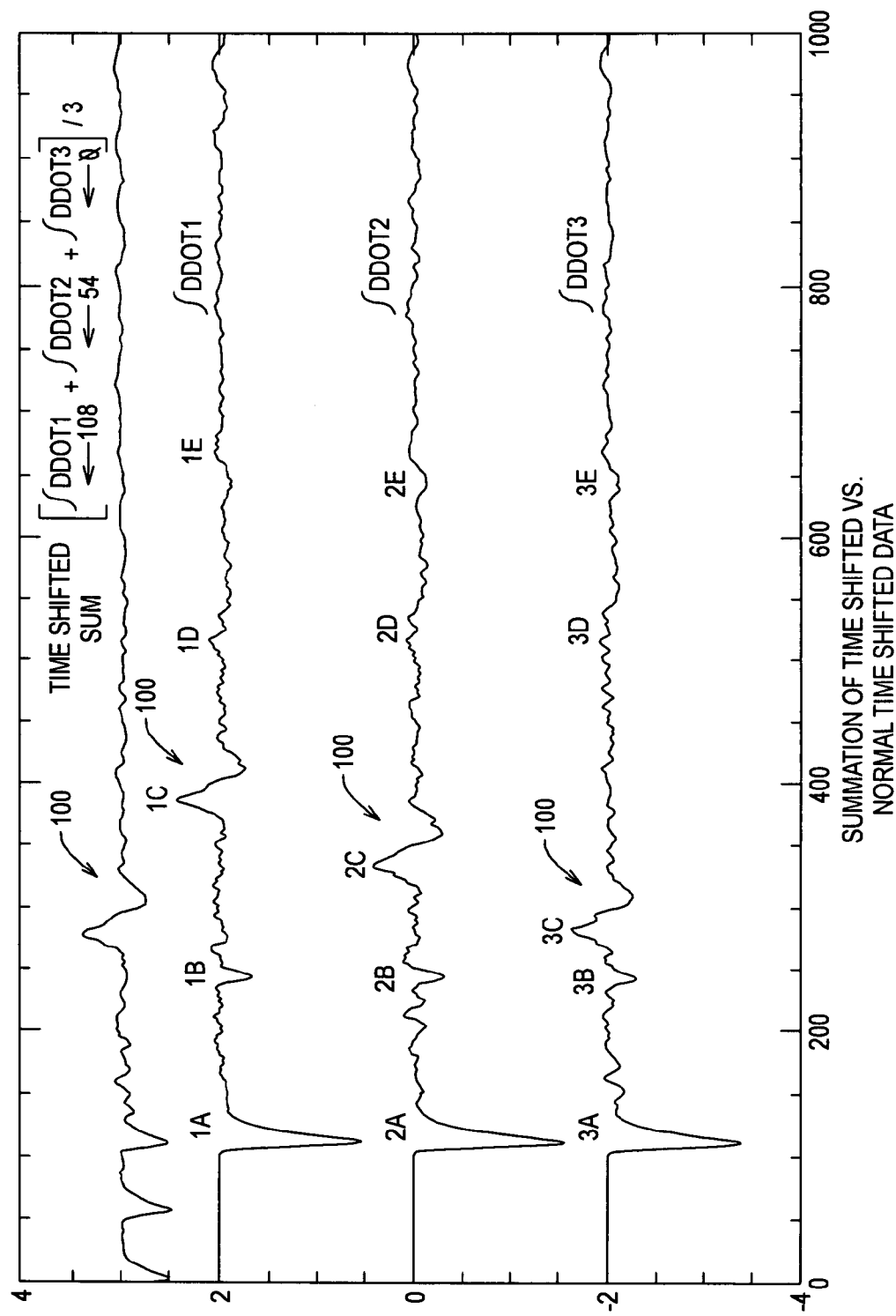
Figure 11:
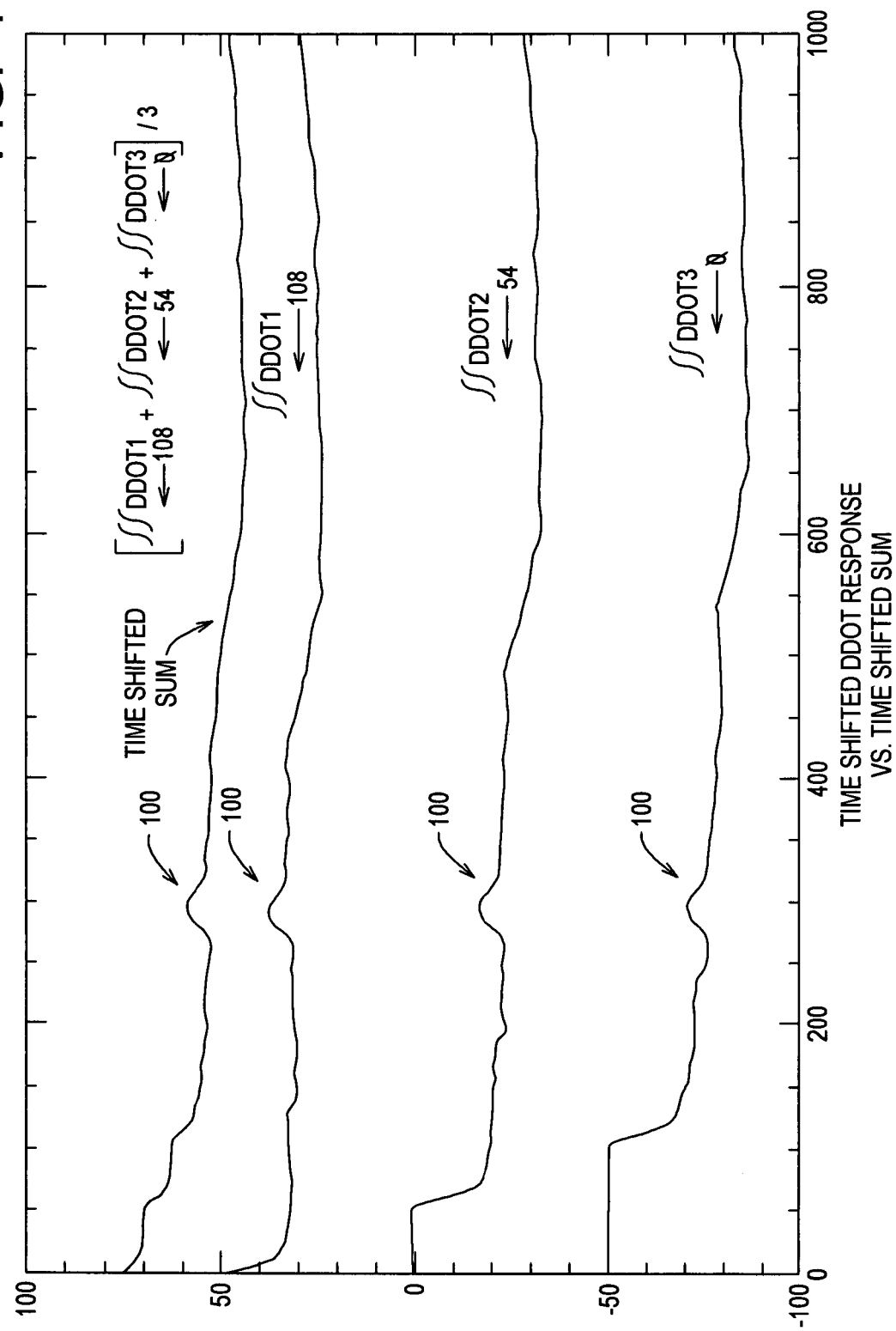
Figure 12:
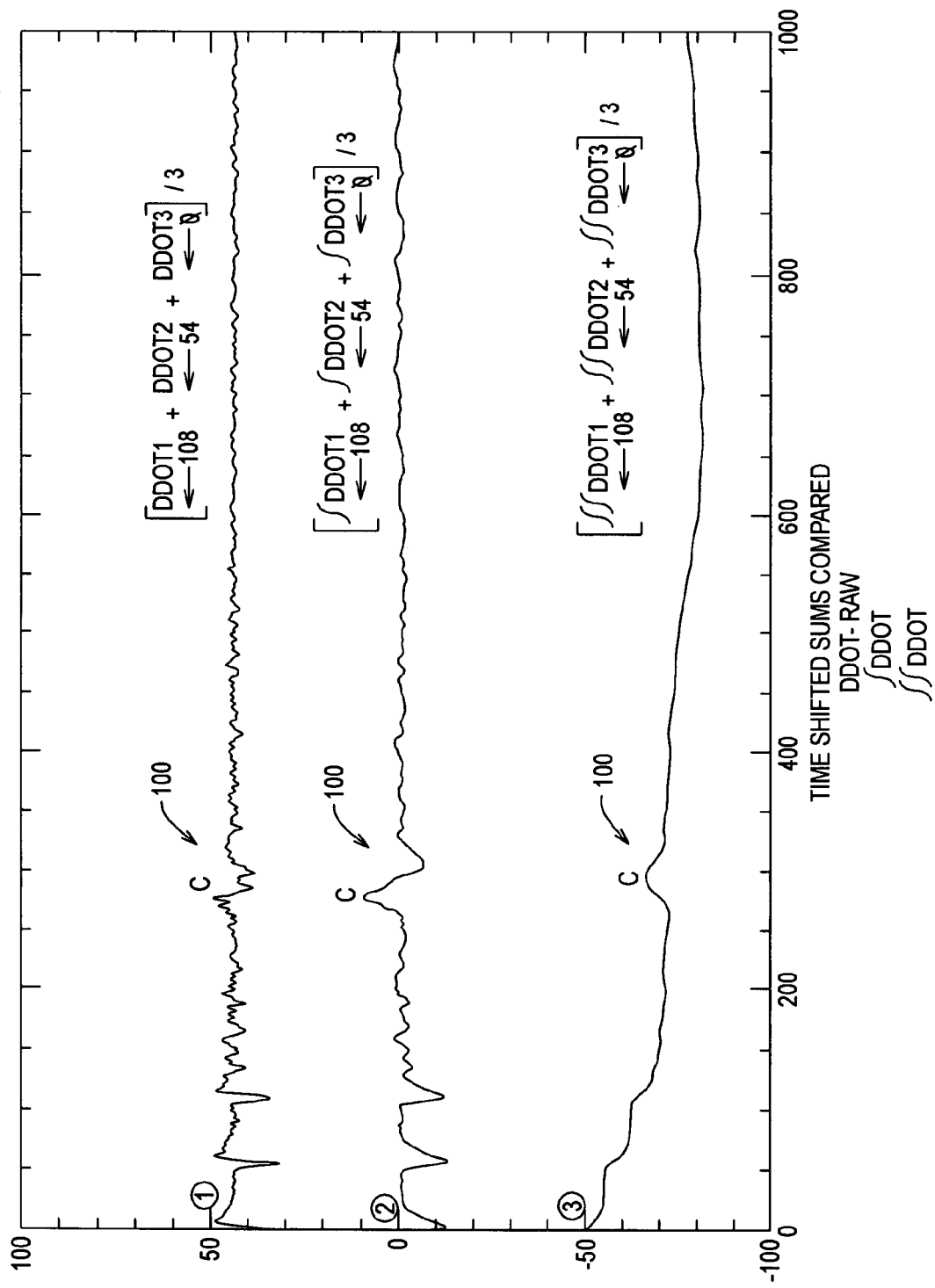
Figure 13:
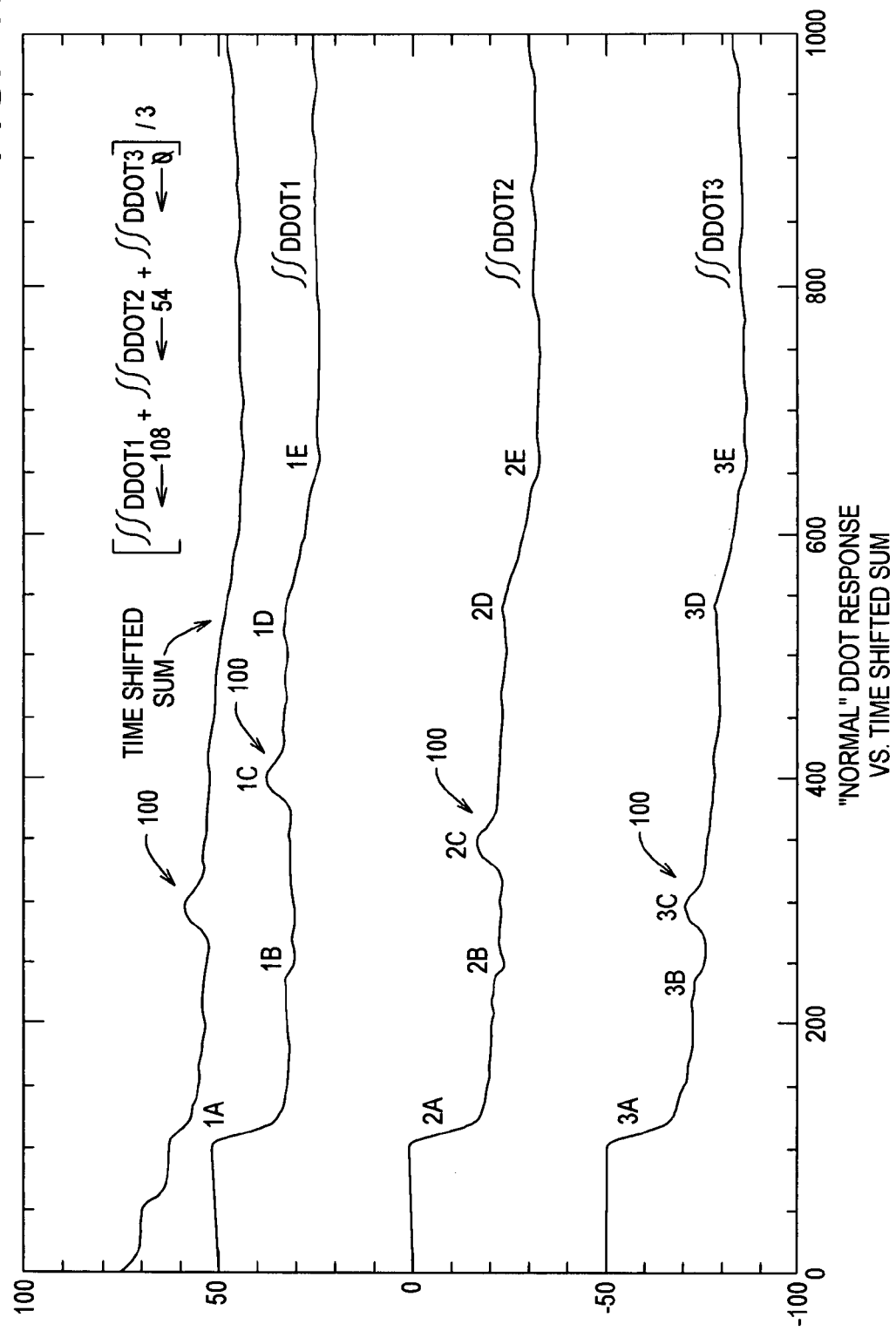

FIG. 8 shows the summation of the time shifted waveforms for the raw data. FIG. 9 shows the summation of the time shifted waveforms for the first integral of the raw data. FIG. 10 illustrates the summation of the time shifted waveforms for the first integral of the raw data. FIG. 11 illustrates the summation of the time shifted waveforms for the second integral of the raw data. FIG. 12 compares the time shifted summation of the raw data, the first integral of the raw data, and the second integral of the raw data. FIG. 13 compares the time shifted sum of the second integral of the raw data with the second integral of the raw data. Note, sequentially, how the information in the test segment to the right of the Ddot probes becomes clear.

The anomaly indicated at 100 in the data depicted in FIGS. 3-5, 7, 10-13 was excavated after the test, and corrosion with 60% metal loss was found at the exact location indicated by the data.

Figure 14:
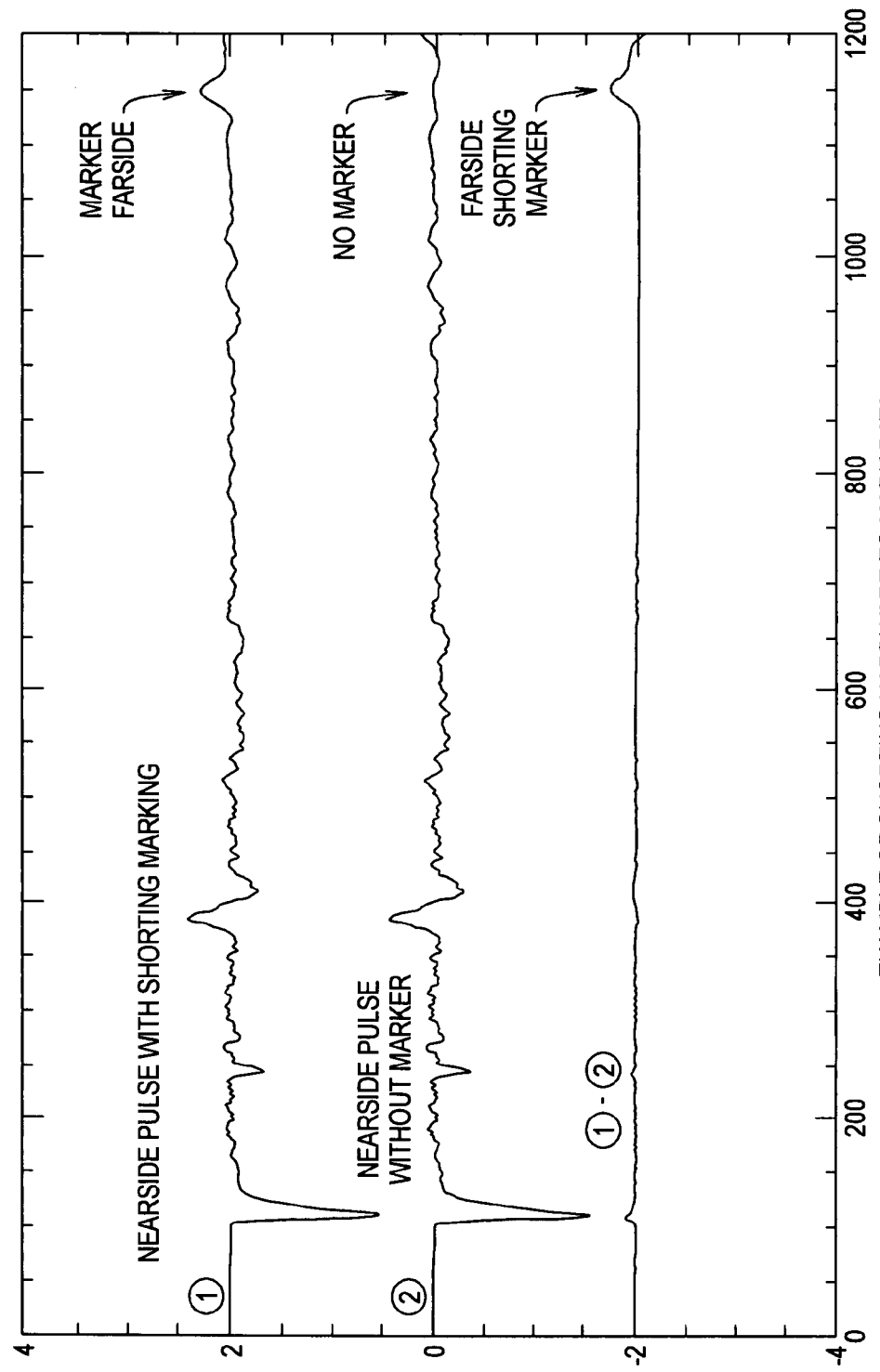

FIG. 14 illustrates the process of using the marker system 56 to help correlate characteristics of the graphs with the pipe under test. The sensor 70 used by the test system 50 may take the form of a self-integrating probe as will be described below and in Exhibit E attached to Provisional Application Ser. No. 60/468,626. Very low level signals, due to improper grounding, or baseline shifts in the acquisition, can cause problems with the data that make it very difficult to interpret. A self-integrating probe can enhance data collection and overcome the problems described above.

In particular, a Ddot probe has been adapted to the tip of a Tektronix FET probe, such as the P6243. Instead of a resistive voltage divider, this system becomes a capacitive voltage divider, and the output of the probe is the first integral of the raw data. Pictures of the working prototype are shown in Exhibit E attached to Provisional Application Ser. No. 60/468,626. In the device shown in that Exhibit E, the short jumpers have been eliminated, and the probe interfaces to a much higher output Ddot with gold plated pins approximately ¼ inch from the pipe jacket. The system shown in that Exhibit E significantly reduces electrical noise sometimes associated with the resistive voltage divider design. This improvement thus helps overcome the difficulties of maintaining laboratory quality measurement in a harsh environment.

Figure 15:
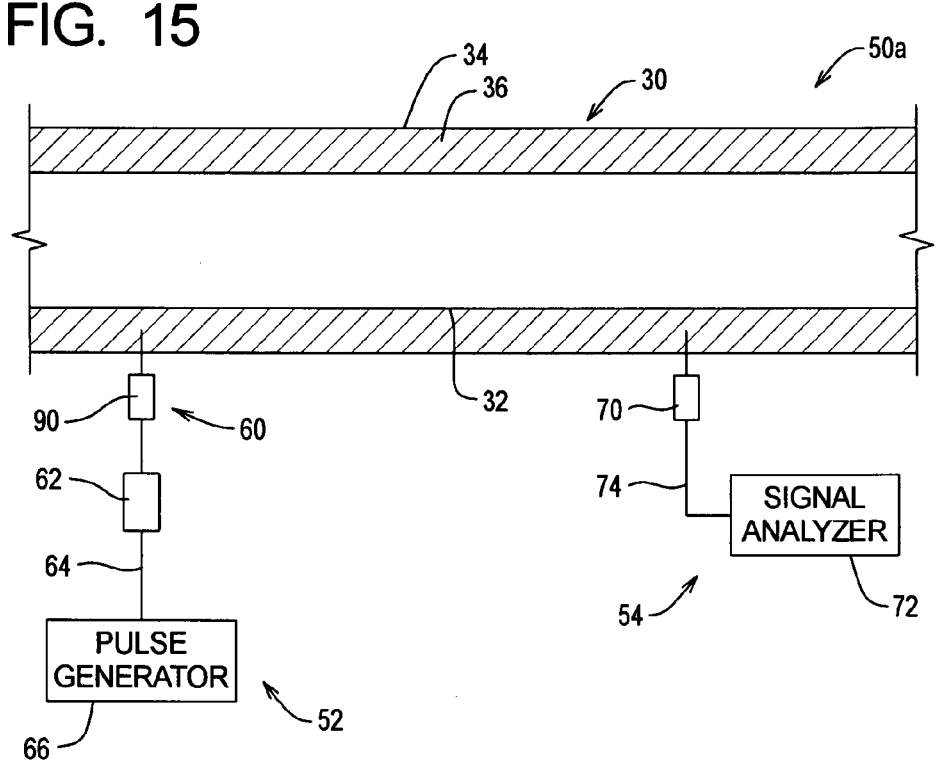
FIGS. 15 and 16 are somewhat schematic views of systems for testing for anomalies on a pipe system.

In addition, shown in FIG. 15 is a modified test system 50a in which the source system 52 uses a Ddot probe 90 as the launcher 60 to launch the pulse onto the pipe 32. The pulse will be applied to the pipe using the Ddot probe 90 as the launcher 60 to inject the signal into the space between the pipe 32 and the external shield 34.

Several advantages are obtained from the use of the Ddot probe 90 as the launcher 60. First, the Ddot probe 90 need not be in resistive contact with the pipe 32.

Another advantage of using a Ddot probe as a pulse launcher 60 is that the pulser 60 can be made an integral part of the launcher 60 with a built in rate generator. This enhances multi-port signal injection without the need for additional signal cables or large battery packs. In very close quarters, such as found in refineries and chemical processing plants, the process would be extremely portable and combined with some of the other improvements, the test results could be almost real time.

A Ddot probe detects the electric field and is omni directional. A Bdot probe detects the magnetic field and is directional. A possible improvement over the use of a self integrating Ddot probe would be to use a Bdot probe, which would automatically detect the direction of the anomaly on the pipe. The use of a Bdot probe may be considered a hardware implementation of what is described above in software and might result in more accuracy, less training of personnel, and higher test production.

Figure 16:
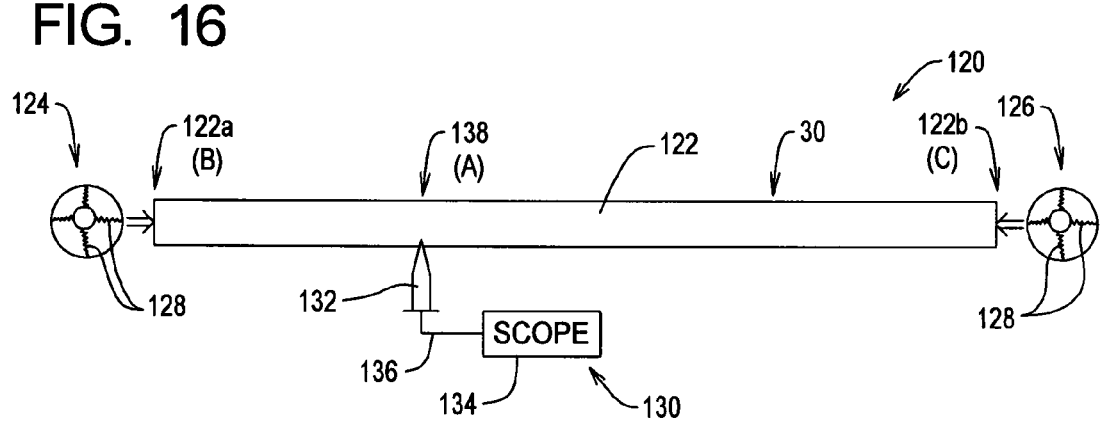

Referring now to FIG. 16, depicted therein is yet another exemplary test system 120 constructed in accordance with, and embodying, the principles of the present invention. The test system 120 is shown testing a segment 122 of insulated, shielded pipe 30 as described above.

As schematically shown in FIG. 16, the example segment 122 of pipe 30 comprises first and second terminating assemblies 124 and 126 formed by four terminating resistors 128. The terminating assemblies 124 and 126 allow the segment 122 to simulate a longer pipe and do not form a part of the present invention. In the example segment 122 depicted in FIG. 16, the segment 122 is approximately 100 feet long.

The test system 120 comprises a signal processing system 130 comprising a probe 132 and a signal analyzer 134 connected by a cable 136. The probe 132 is arranged at a test location 138 spaced between the ends 122a and 122b of the segment 122. In particular, the test location 138 is approximately twenty-two feet from the first segment end 122a and approximately seventy-eight feet from the second segment end 122b. The test location 138 and first and second segment ends 122a and 122b will be referred to as points A, B, and C, respectively.

The example probe 132 functions as both a source of a pulse or series of pulses applied to the pipe system 30 and as a sensor for receiving any reflected pulses arising from features or anomalies of the pipe system 30. The sensor portion of the probe 132 transmits any such reflected pulses to the signal analyzer 134 through the cable 136. The probe 132 further generates a trigger pulse that is sent to the signal analyzer 134 through the cable 136 to facilitate analysis of the reflected pulses.

Figure 17:
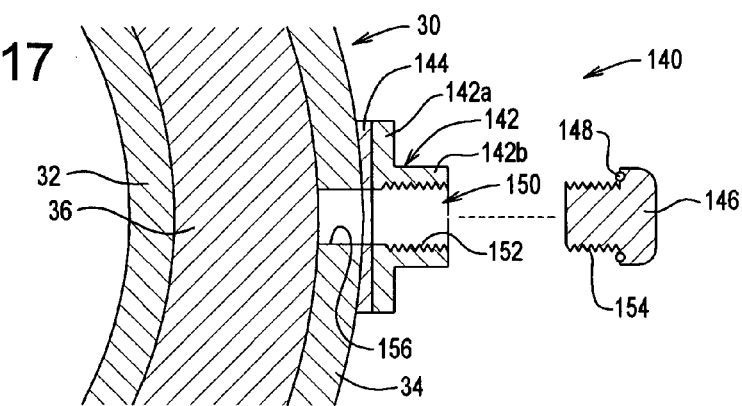
FIGS. 17-19 are partial cutaway views depicting an example probe system that may be used by the testing system of FIG. 16.
Figure 18:
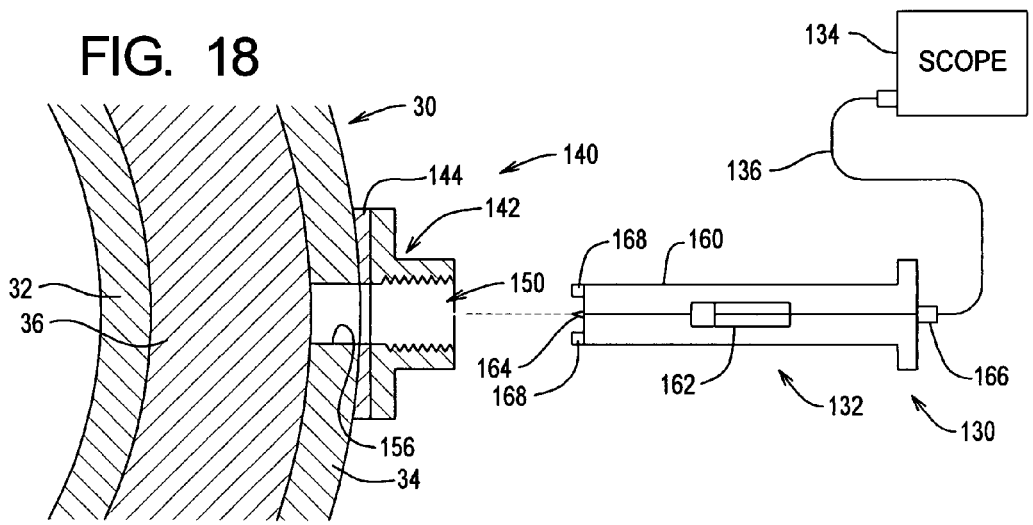
Figure 19:
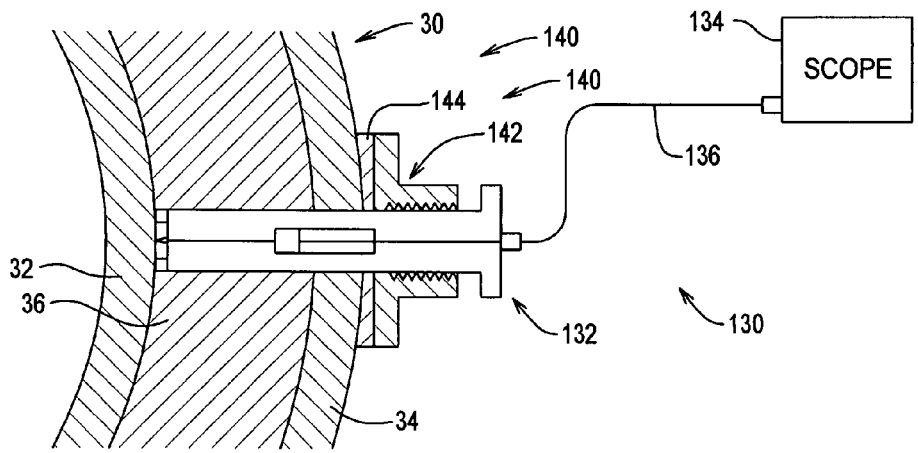

Referring now to FIGS. 17-19, depicted in detail therein is an example embodiment of the probe 132 and an attachment system 140 for detachably attaching the probe 132 to the pipe 30.

As shown in FIG. 17, the example attachment system 140 comprises a base member 142, a seal 144, a cap member 146, and an O-ring 148. The base member 142 defines a flange portion 142a and a mounting portion 142b. The mounting portion 142b defines a passageway 150. The passageway 150 defines a first threaded surface 152, while the cap member 146 defines a second threaded surface 154. The cap member 146 may be detachably attached to the base member 142 using the threaded surfaces 152 and 154, but other attachment systems can be used.

The flange portion 142a of the base member 142 is attached to the shielding 34 by screws, bolts, adhesives, or the like. A shield opening 156 is formed in the shielding 34 to allow access to the pipe 32 through the passageway 150. The seal 144 may be formed, as examples, by a separate gasket or a layer of hardened adhesive between the base member 142 and shielding 34. The mounting portion 142b of the base member 142 defines the passageway 150 and extends outwardly away from the pipe system 30.

In a first configuration, the cap member 146 is detachably attached to the base member 142 such that the cap member 146 closes the passageway 150; the seal 144 and O-ring 148 inhibit entry of moisture into the pipe system 30 through the shield opening 156 in this first configuration. In a second configuration, the cap member 146 is detached from the base member 142 such that pipe 32 is accessible through the passageway 150 and the shield opening 156.

As perhaps best shown in FIG. 18, the probe 132 comprises a housing 160, electronics 162, a pipe terminal 164, a cable terminal 166, and alignment projections 168. The electronics 162 are mounted within the housing 160. The pipe terminal 164 is supported at one end of the housing 160. The cable terminal 166 is also supported by the housing 160. The pipe terminal 164 and cable terminal 166 are electrically connected to the electronics 162.

The housing 160 is sized and dimensioned to be inserted at least partly through the passageway 150 and the shield opening 156. Although other shapes may be used, the passageway 150, shield opening 156, and housing 160 are at least partly cylindrical in the example signal processing system 130.

To use the signal processing system 130, the probe housing 160 is inserted through the passageway 150 and shield opening 156 until the pipe terminal 164 comes into contact with the pipe 32. The alignment projections 168 also engage the pipe 32 to center the pipe terminal 164 on the curve of the pipe 32. Additionally, a fixing mechanism may be used to fix the position of the probe housing 160 relative to the base member 142 when the pipe terminal 168 is in a desired relationship with the pipe 32. For example, a set screw or the like may extend through the mounting portion 142b of the base member 142. Rotating the set screw relative to the base member 142 displaces the set screw towards the housing 160 to force the housing 160 against the threaded surface 152 to secure the housing 160 relative to the base member 142.

The electronics 162 are then activated to apply an electrical pulse to the pipe 32 through the pipe terminal 164. Applied signals will thus propagate in both directions away from the test location 138. The pulse generator may take the form of a simple timing circuit that generates an electrical pulse; the electrical pulse may take on a number of forms, but the example electronics 162 generates a step function waveform. The electronics 162 further comprise an impedance matching resistor arranged between the pulse generator and the pipe terminal 164.

As described above, the applied signals traveling away from the test location 138 may encounter anomalies and features of the pipe system 130 that will cause at least one reflected signal to travel back towards the test location 138. The probe 132 is further capable of detecting at least some of the reflected signals as they pass through the test location 138. In particular, the probe 132 may directly sense the reflected signals through ohmic contact between the pipe terminal 164 and the pipe 32. In this case, a simple resistive divider probe may be connected to the pipe terminal 164. Alternatively, a Ddot probe may be arranged within the housing 160 adjacent to the pipe terminal 164 to introduce reflected signals into and/or sense reflected signals in the pipe system 30.

In any case, the electronics 162 contains circuitry as necessary to introduce the applied signals into the pipe 32 and sense the reflected signals traveling through the test location 138. The reflected signals sensed by the electronics 162 are applied to the cable terminal 166 for transmission to the signal analyzer 134. The electronics 162 further may generate a trigger signal corresponding to the generation of the electrical pulses applied to the pipe 32. The trigger signal is also applied to the cable terminal 166 to facilitate analysis of the reflected signals by the signal analyzer 134.

Figure 20:
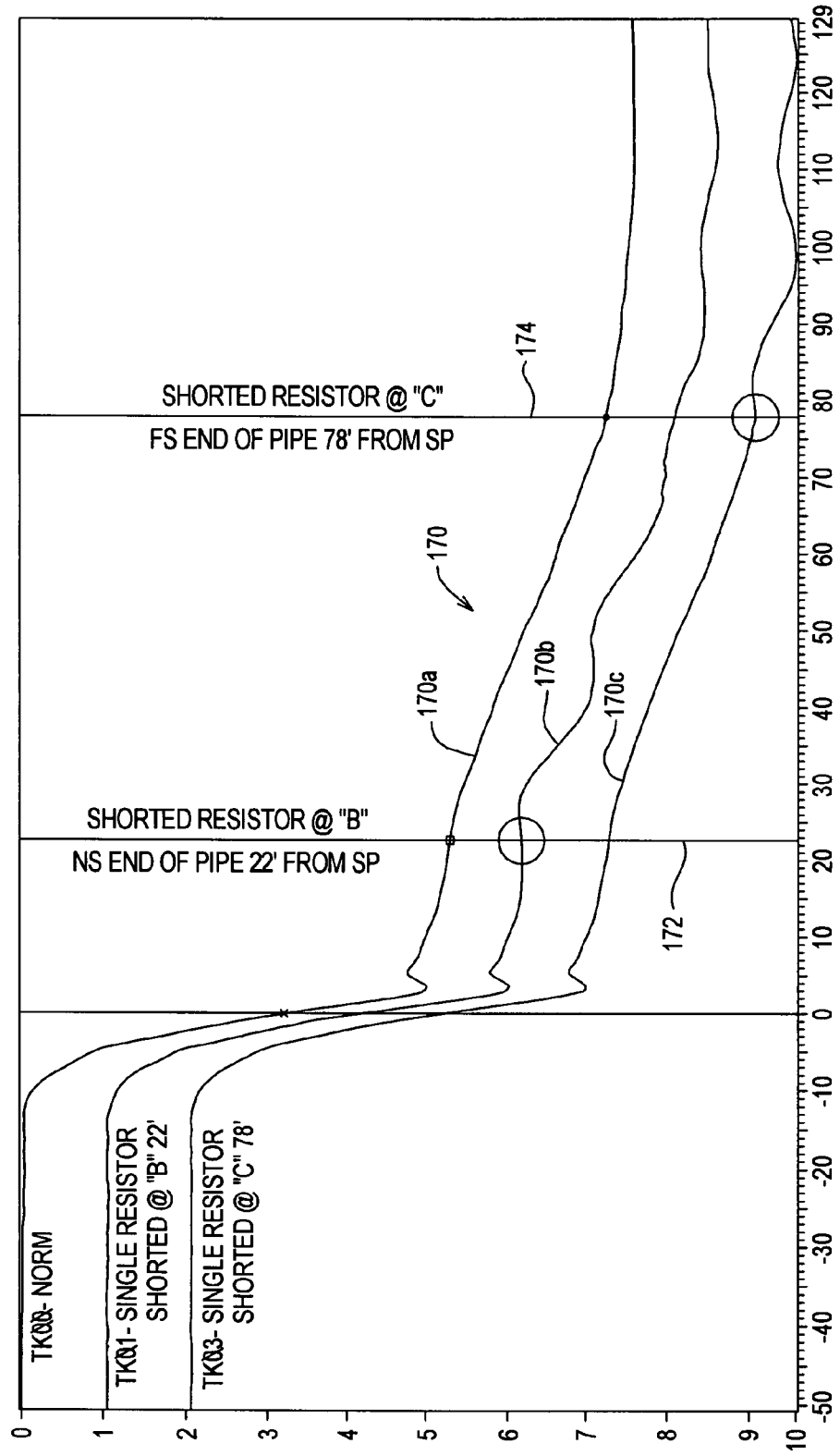
FIG. 20 is a graph plotting data obtained using the system depicted in FIG. 16.

Referring now to FIG. 20, depicted therein is a graph 170 representing the reflected signals received using the signal processing system 130 on the pipe segment 120 illustrated in FIG. 16. The graph 170 contains three traces 170a, 170b, and 170c.

The trace 170a depicts the signal measured by the signal analyzer 134 with the standard test system as depicted in FIG. 16 (i.e., four terminating resistors 128 connected to each end 122a and 122b). The standard test system generally corresponds to a good pipe of infinite length. After an initial steep drop and rise in the time interval represented by approximately 0 to 3 on the X-axis, the trace 170a begins a gradual, relatively featureless decline.

The trace 170b illustrates the signal measured by the signal analyzer 134 with one of the terminating resistors 128 shorted on the first end 122a of the segment 122. The trace 170b is similar to the trace 170a in the time interval represented by approximately 1-15 of the X-axis. In the time interval represented by approximately 15-30 on the X-axis, the slope of the trace 170b increases and becomes positive. In the time interval represented by approximately 30-130, the trace 170b generally declines in a manner similar to the trace 170a but exhibits change in slope similar to those associated with an oscillation. A line 172 in FIG. 20 illustrates that the scale associated with the X-axis has been selected such that the initial rise in the slope of the trace 170b corresponds to the location 22 feet away.

The trace 170c illustrates the signal measured by the signal analyzer 134 with one of the terminating resistors 128 shorted on the second end 122b of the segment 122. The trace 170c is similar to the trace 170a in the time interval represented by approximately 1-75 of the X-axis. In the time interval represented by approximately 75-83 on the X-axis, the slope of the trace 170c increases and becomes positive. In the time interval represented by approximately 83-130, the trace 170c generally declines in a manner similar to the trace 170a but exhibits change in slope similar to those associated with an oscillation. A line 174 in FIG. 20 illustrates that the scale associated with the X-axis has been selected such that the initial rise in the slope of the trace 170c corresponds to the approximately location 78 feet away.

Analyzing both traces 170b and 170c in the context of the scale selected for the X-axis illustrates that the anomalies in the traces 170b and 170c generally correspond to the anomalies in the pipe segment 122 at the first and second ends 122a and 122b thereof, respectively. The test system 120 thus effectively determines differences in impedance introduced in the test segment 122. The Applicants believe that the test system 120 can thus be used to determine differences in impedance caused by anomalies in a pipe system such as corrosion.

In addition, signal processing techniques described above with reference to FIGS. 2-14 may also be applied to the traces 170b and 170c. For example, subtracting the trace 170b from the trace 170a will result in a series of spikes, with the first such spike being associated with the anomaly at the first end 122a of the pipe segment 122. Additional signal processing techniques might allow the traces to be examined by relatively low-skilled technicians or even automated such that the detection of anomalies may be performed by a computer.

The example pipe segment 122 depicted in FIG. 16 is a very simple case of a straight pipe with no features such as terminations, corners, changes in diameter, or the like. In the real world, the pipe system 30 may be used to form a long pipeline or an extensive network of interconnected pipes at a manufacturing site. In such a larger pipe system, features of the pipe in good condition may cause reflected signals that may not be easily distinguishable from reflected signals generated by anomalies, such as corrosion, associated with failed or failing pipe.

To facilitate the recognition of features associated with failed or failing pipe, traces may be generated for pipe in known good condition at one point in time and compared with traces generated at one or more later points in time. Changes in the traces over time can be monitored. If these changes fall outside predetermined parameters, the pipe under test can be checked for failure at locations associated with changes in the trace.

Also, to test discrete portions of the pipe system 30 in a larger system, the probe 132 may be detachably attached in sequence to one or more discrete test locations in the pipeline or network of pipes. FIGS. 17-19 describe one possible attachment system 140 that may be used for this purpose. Alternatively, probes like the probe 132 may be permanently attached to one or more test locations located along the pipeline or throughout the pipe network. In this case, the probe 132 may be provided with an access port, memory, and/or telemetry systems for simplifying the process of obtaining data.

Yet another example of a system and method of remotely analyzing an elongate conductive member for anomalies will now be described with reference to FIGS. 21-26. In particular, depicted in FIG. 23 is an example test system 220 that may be used to determine the presence and/or location of anomalies along an elongate conductive member 222.

Like the systems and methods described above, the test system 220 employs the backward reflection of an electromagnetic pulse wave propagating along the elongate conductive member 222. However, the Applicants have recognized that, for certain anomalies, the effectiveness of the systems and methods of the type generally described above can be improved by perturbing the elongate conductive member 222 as the electromagnetic pulse is applied thereto.

Certain types of anomalies are typically of more interest than other types of anomalies. In the following discussion, the term "spurious anomalies" will refer to anomalies in an elongate conductive member that are not of interest. Backscattered electromagnetic energy from spurious anomalies can obscure backscattered electromagnetic energy from anomalies of interest such as corrosion of a pipe member.

In the example test system 220 described with respect to FIGS. 21-26, the elongate conductive member 222 is a pipe member 230 forming part of a pipe system 232. The pipe member 230 may be buried or unburied or cased or uncased. The pipe system 232 may comprise or be influenced by pipe components such as flanges, insulation, and shielding, environmental conditions such as dirt and ground water, and anomalies on the pipe such as iron oxide (rust).

The example pipe member 230 under test is a 4-inch direct buried pipe two-hundred sixteen feet in length. The pipe member 230 defines first and second ends 234 and 236. First and second pipe portions 240 and 242 are located seventy-five and fifty feet, respectively, from the second end 236. In the example pipe system 232, the pipe portions 240 and 242 are known to be corroded. The pipe system 232 further defines first, second, and third test locations 244, 246, and 248 at which test equipment may be located as will be described in further detail below. The first and second test locations 244 and 246 are arranged at the first and second ends 234 and 236 of the pipe, while the third test location 248 is located along the pipe between the first and second ends 234 and 236.

The example third test location 248 happens to be located seventy-two feet from the second end, or between the first and second pipe portions 240 and 242. The physical relationship between third test location 248 and the corroded pipe portions 240 and 242 need not be predetermined or even known in advance.

The corroded pipe portions 240 and 242 would be considered anomalies of interest in the context of the pipe member 230. The following anomalies might also be considered anomalies of interest: stress cracks, deposits of magnetic oxides (rust), metal fatigue, improper welds, and regions of active electrolysis that have not yet progressed to visible corrosion. In the pipe system 232, spurious anomalies might include non-structural dents and, in the case of direct buried pipe, changes in soil composition, roots, debris, rocks, ground water.

The Applicants have recognized that the electromagnetic properties of certain anomalies of an elongate conductive member 222 are nonlinear, and this fact can be used to determine whether backscattered electromagnetic energy is caused by anomalies of interest or by spurious anomalies. Anomalies having nonlinear electromagnetic properties will be referred to herein as nonlinear anomalies, and certain nonlinear anomalies are anomalies of interest.

The Applicants have further recognized that perturbing the pipe member 230 by, for example, modifying the electric or magnetic field of the pipe member 230 modifies the electromagnetic properties of the pipe member 230 at the location of nonlinear anomalies. The modified electromagnetic properties of the pipe member 230 at the location of the nonlinear anomalies result in differences in the backscattered electromagnetic energy signals reflecting from the nonlinear anomalies. These differences can be detected and used to determine both the presence of the nonlinear anomaly and, in conjunction with other characteristics of the pipe system 232 that will be described further below, the location of the nonlinear anomaly.

In the specific case of corrosion, electrolytic activity associated with active corrosion can give nonlinear resistance. For direct buried pipe in contact with moist earth, the surface resistivity in regions of active corrosion can vary with the applied electric field in a nonlinear manner; that is, the ratio of voltage-to-current is not a constant. In this case, the perturbing voltage modifies the local impedance directly by changing the pipe-to-soil resistance at the site of active corrosion. Changes in pipe-to-soil resistance at the site of active corrosion allow the corrosion to be detected in buried pipes from a remote location.

In addition, areas of active corrosion can be located by measuring time-of-flight for those returns that change when the perturbation is changed. In this context, an electromagnetic pulse, referred to herein as the source pulse, is applied to the conductive member 222 such that the pulse travels through anomalies on the conductive member. The anomalies cause a portion of the electromagnetic energy of the source pulse to be reflected back along the conductive member. The reflected energy will be referred to herein as the return signal.

In the case of a bias current applied to a direct buried pipe, the response of the nonlinear properties in regions of corrosion can be delayed in time by several seconds from the application of the perturbing field. This delay for polarization and depolarization to occur can be used to isolate areas of active corrosion. The charge time for polarization and decay time for depolarization depend on the degree and type of corrosion. Various sources of corrosion can be identified by observing changes in the backscattered electromagnetic signal after the perturbing field is reversed, turned-on, or turned-off. In addition, the polarization and depolarization times were different for corroded and non-corroded pipe.

The perturbation applied to the elongate conductive member 222 can be formed by methods other than simply applying a voltage or current to the conductive member. For example, a magnet held in proximity to the conductive member may perturb the conductive member at the anomaly.

The Applicants further recognized that the resistance of corroded pipe has a nonlinear current-voltage relationship that is quite different from the current-voltage relationship of clear, un-corroded conductive members. This difference allows return signals from anomalies of interest to be identified in the presence of return signals from spurious anomalies.

The return signals may further be processed using one or more data processing techniques to determine which return signals are associated with anomalies of interest. One useful data processing technique is to obtain a plurality of sets of raw data for a particular set of conditions and obtain an averaged set of raw data by averaging the plurality of individual sets of raw data.

As another example, a sequence of return signals may be detected for a particular set of perturbation conditions. The sequence of return signals may be time-shifted and/or added to or subtracted from returns generated for different sets of perturbation conditions. This technique can be used to separate return signals coming from opposite directions along the conductive member. In addition, the use of separate electric and magnetic field probes (D-Dot and B-Dot sensors) allow the direction of a return pulse to be determined based on a single point measurement with time shifted subtraction.

Referring now more specifically to FIGS. 21 and 22, these figures illustrate that the example anomalies at the corroded pipe portions 240 and 242 alter the electromagnetic characteristics of the pipe member 230. In particular, FIG. 21 depicts an example test set-up 250 comprising a DC power supply 252, an ammeter 254, and a volt meter 256. A grounding electrode (anode) 258 is connected to one terminal of the DC power supply 252 and may be formed by the anode of a conventional cathodic protection system used to inhibit corrosion in pipe systems. The other terminal of the DC power supply 252 is connected to the third test location 248 through the ammeter 254.

The DC power source 252 may take the form of a constant current or constant voltage source that may be selectively switched, or pulsed, on or off to perturb the elongate conductive member 222. If a bias current is employed on the pipe, the resulting magnetic field can affect the magnetic properties of Ferro-magnetic iron-oxide (rust) at the corrosion site. The magnetic permeability can change depending on the strength of the magnetic field caused by the externally applied current. The bias current thus creates a nonlinear magnetic response of the material caused by the applied perturbing field.

In a similar manner, a thin film coating of metallic oxide occurring at the site of active corrosion in the presence of water can change the thickness of the film and resulting local capacitance due to the presence of the electric field from an externally applied perturbing voltage source. When either the local inductance or local capacitance of a conductive member is changed, changes in the backscattered electromagnetic pulse signal can be observed. These changes can uniquely identify areas of corrosion.

The example DC power supply 252 is configured to apply a DC voltage to the pipe member 230 at the third test location 248. The example DC power supply 252 is a capable of applying DC voltages and currents to the pipe member 230 at different voltage and current levels and different polarities. When the DC power supply 252 is operated, the voltage measured by the volt meter 256 may be divided by the current measured by the ammeter 254 to obtain the resistance of the pipe member 230.

Referring now to FIG. 22 of the drawing, depicted therein is the plot 260 of pipe-to-soil resistance versus time obtained using the test system 250. The resistance was obtained by dividing the measured voltage by the injected current. The plot 260 comprises a first main portion 262 associated with a first current level, a second main portion 264 associated with a second current level, and a third main portion 266 associated with a third current level. The polarity of the DC signal is altered within each of the three main portions 262, 264, and 266 such that the plot further comprises first and second sub-portions 262a,b, 264a,b, and 266a,b within each of these plot portions 262, 264, and 266.

Comparing the first sub-portions 262a, 264a, and 266a of the first, second, and third main portions 262, 264, and 266 illustrates that the resistance as calculated from the measured current and voltage differs with differing magnitudes and polarities associated with these sub-portions. Similarly, comparing the second sub-portions 262b, 264b, and 266b of the main portions 262, 264, and 266 illustrates that resistance is also different at the different current levels and polarities associated with these sub-portions. Finally, comparing the first sub-portions 262a, 264a, and 266a with the second sub-portions 262b, 264b, and 266b corresponding thereto illustrates that the resistance associated with the positive and negative polarities of the applied DC signal is different.

The comparisons of the various portions of the plot 260 depicted in FIG. 22 thus clearly indicate that the resistance of the pipe member 230 is nonlinear. Although only resistance data is plotted in FIG. 22, FIGS. 21 and 22 thus illustrate that certain types of anomalies, including the corrosion at locations 240 and 242, have unique, nonlinear electromagnetic characteristics. In the case depicted and described with reference to FIGS. 21 and 22, the nonlinear electromagnetic characteristics of the corrosion at locations 240 and 242 alter the resistance of the pipe member 230 at these locations 240 and 242 when perturbed by the application of a DC voltage signal to the pipe member 230.

Figure 23A:
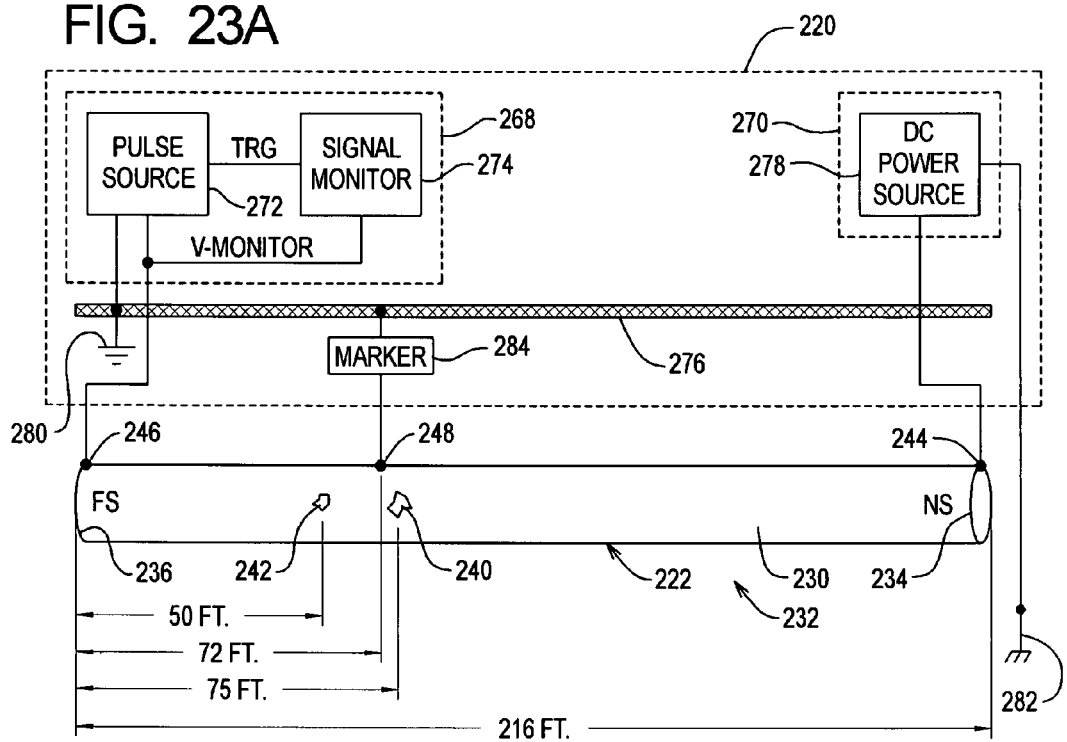
FIG. 23A-C are schematic block diagrams depicting example configurations of a system for conducting time domain impedance analysis of an elongate conductive member in accordance with the principles of the present invention.
Figure 23B:
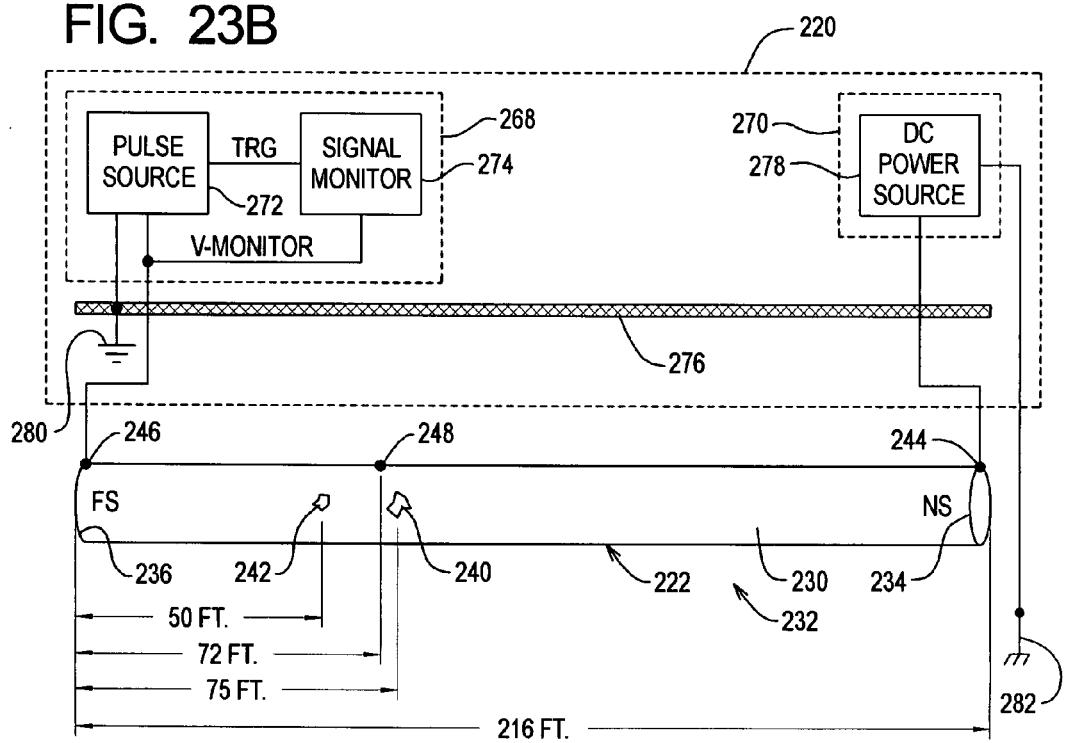
Figure 23C:
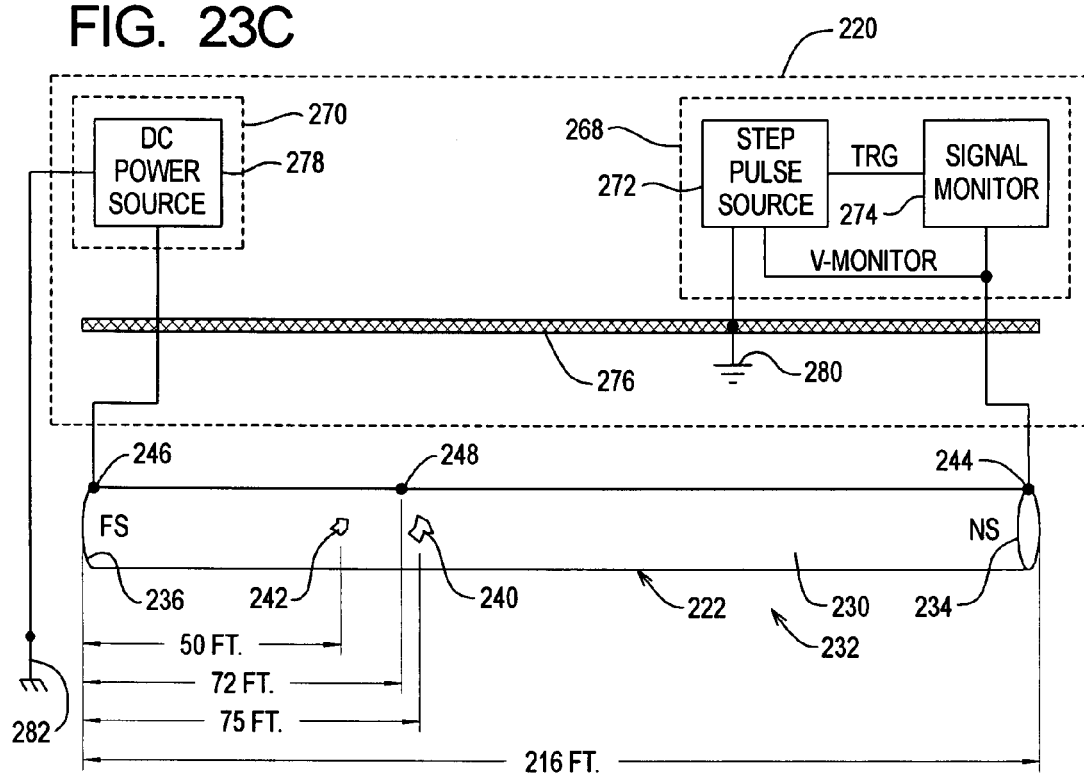

Referring now to FIGS. 23A-C, the test system 220 depicted therein will be described in further detail. The example test system 220 uses the phenomenon described with reference to FIGS. 21 and 22 to identify both the presence and location of the anomalies at the locations 240 and 242 on the pipe member 230.

The test system 220 comprises an exciting system 268 and a perturbation system 270. The exciting system 268 comprises a pulse source 272, a signal monitor 274, and a grounding screen 276. The perturbation system 270 comprises a DC power supply 278.

The pulse source 272 is a pulse generator capable of generating an electromagnetic pulse that may be applied to the conductive member 222. The example pulse source 272 may generate pulses of various magnitudes and shapes. For insulated shielded pipes, a pulse having an amplitude of approximately 500 volts and a pulse-width of approximately two nanoseconds may be used. For direct buried pipe, a step function voltage having a similar magnitude may be used. Other waveforms, such as unipolar, bipolar, and oscillatory waveforms, may be used depending upon the environmental conditions. Swept frequency continuous wave sinusoidal frequency sources may also be used to excite the conductive member 222. In this case, Fourier transform analysis may be used to convert the frequency domain data to time domain data using FFT processing, either directly on a frequency domain network analyzer or on a computer.

The signal monitor 274 is configured to monitor and record a test signal V-MONITOR present at either the first test location 244 (FIG. 23C) or the second test location 246 (FIGS. 23A-B). The signal monitor 274 further operates based on a trigger signal TRG generated by the step pulse source 272.

The grounding screen 276 may be formed of any element, such as a physical screen, wire, rod, or anode, capable of forming a counterpoise or return conductor. The grounding screen 276 or other return conductor need not extend the full length of the pipe. A short length of screen mesh lying on the ground directly above the end of the pipe from which the pulse is launched has been found to be sufficient. The return conductor thus need only be of sufficient length to allow the pulse source 272 to launch the electromagnetic pulse at either the first test location 244 (FIG. 23C) or the second test location 246 (FIGS. 23A-B).

Like the DC power supply 252 described above, the DC power supply 278 is capable of applying DC voltages and currents to the pipe member 230 at different voltage and current levels and different polarities.

The example test system 220 further comprises an optional first grounding electrode 280 and second grounding electrode 282. The first grounding electrode 280 may be formed by an electrode, wire, or stake connected between ground and the step pulse source 272, between ground and the grounding screen 276, or between ground and both the step pulse source 272 and the grounding screen 276.

The second grounding electrode 282 is connected to one terminal of the DC power supply 278 and may be formed by the grounding terminal (anode) of a conventional cathodic protection system used to inhibit corrosion in pipe systems. The other terminal of the DC power supply 278 is connected to either the first test location 244 (FIGS. 23A-B) or the second test location 246 (FIG. 23C).

In FIGS. 23A-C, the first and second ends 234 and 236 of the pipe member 230 are labeled "NS" and "FS" and, in the following discussion, will be referred to as the near side end and far side end, respectively, of the pipe member 230. The terms "near side" and "far side" are completely arbitrary and are used by convention to identify the first and second ends of the particular pipe member 230 being tested by the test system 220.

Referring initially to FIG. 23A, that figure illustrates that the configuration of the test system 220 depicted therein further comprises a marker element 284 temporarily connected between the third test location 248 and the grounding screen 276. The marker element 284 may take the form of a diode or short circuit connection temporarily connected to the pipe member 230 at a known location. If the physical location of the third test location 248 is known with respect to the pipe member 230, the marker element 284 may be used to calibrate the wave speed in the particular environment for the purpose of distance calibration.

The use of a diode as the marker element 284 in connection with the elongate conductive member 222 also allows a non-linearity to be remotely introduced into the system incorporating member 222 simply by applying a remote biasing DC voltage to turn the diode on or off.

Referring now to FIG. 23B, depicted therein is a configuration of the test system 220 similar to that depicted in FIG. 23A, except that no marker element 284 is connected to the third test location 248. In the configuration depicted in FIG. 23B, the test system 220 is used generally as follows.

The pulse source 272 of the exciting system 268 selectively launches one or more electromagnetic pulses from the far side 236 such that the electromagnetic pulses propagate at least from the far side 236 towards the near side 234. When appropriate, the DC power supply 278 of the perturbation system 270 perturbs the conductive member by selectively applying one or more DC voltage levels and/or polarities to the conductive member 222 at the near side 234. The signal monitor 274 detects return signals caused by the backscatter of electromagnetic pulses traveling along the conductive member 222. This backscatter occurs when the pulses pass through anomalies on the conductive member 222. In the example system 220, the return signals are voltage signals, and these voltage signals are correlated to conductor impedance at the location where the backscatter occurs.

The operation of the pulse source 272 is timed in relation to the operation of the DC power supply 278 such that the signal monitor 274 collects sets of raw data generated under different operating conditions of the test system 220. For example, a first set of raw data may be collected with the DC power supply in an off position. A second set of raw data may be collected after the DC power supply is operated to place a positive DC signal on the conductive member 222. A third set of raw data may be collected after the DC power supply is operated to place a negative DC signal on the conductive member 222.

The sets of raw data may be analyzed directly for signatures associated with anomalies. The sets of raw data may additionally be processed and then analyzed. For example, the first set of raw data may be subtracted from the second or third sets of raw data to illustrate differences in the data associated with the perturbations caused by the perturbation system 270.

Referring now to FIG. 24 of the drawing, that figure contains a data trace 290 of the data obtained using the test system 220 configured as shown in FIG. 23C. The data trace 290 represents samples of the return signals detected with the DC power supply off subtracted from corresponding return signals detected with the DC power supply set to a positive voltage. More specifically, the return signal detected with the DC power supply off is subtracted from the return signal detected with the DC power supply applying a positive voltage to the pipe member 230 to obtain processed data.

The vertical scale of the trace 290 thus corresponds to changes in time-resolved impedance resulting from the subtraction of two sets of raw data representing return signals. The horizontal scale is calibrated in feet based on the wave propagation speed of the pipe measured using the calibration marker as described with reference to FIG. 23A. For reference, FIG. 24 further includes a trace 292 that illustrates the processed data obtained using the marker element 284 as described above. The trace 292 illustrates an impedance change for the calibration marker located at the third test location 248.

The trace 290 illustrates a first impedance change at a trace portion 290a and a second impedance change at a trace portion 290b. These impedance changes generally correspond to the locations fifty feet and seventy five feet, respectively, from the far side 236. These impedance changes thus illustrate that the test system 220 of the present invention detects and identifies corrosion at on the conductive member 222 from a remote location.

Raw data was similarly taken with the test system 220 configured as illustrated in FIG. 23C. In FIG. 23C, the pulse source 272 of the exciting system 268 selectively launches one or more electromagnetic pulses from the near side 234 such that the electromagnetic pulses propagate at least from the near side 234 towards the far side 236. When appropriate, the DC power supply 278 of the perturbation system 270 perturbs the conductive member 222 by selectively applying one or more DC voltage levels and/or polarities to the conductive member 222 at the far side 236.

As in the case depicted in FIG. 23B, the operation of the pulse source 272 is timed in relation to the operation of the DC power supply 278 such that the signal monitor 274 collects sets of raw data generated under different operating conditions of the test system 220.

Referring now to FIG. 25 of the drawing, that figure contains a data trace 294 of the data obtained using the test system 220 configured as shown in FIG. 23C. The data trace 294 represents samples of the return signals detected with the DC power supply off subtracted from corresponding return signals detected with the DC power supply set to a positive voltage. Processed data is obtained by subtracting the return signal detected with the DC power supply off from the return signal detected with the DC power supply applying a positive voltage to the pipe member 230. For reference, FIG. 24 further includes a trace 296 that illustrates the processed data obtained using the marker element 284 as described above. The trace 296 illustrates an impedance change at 296a for the calibration marker located at the third test location 248.

The trace 294 illustrates a first impedance change at a trace portion 294a and a second impedance change at a trace portion 294b. These impedance changes generally correspond to the locations fifty feet and seventy five feet, respectively, from the far side 236. These impedance changes corroborate the conclusions reached from analyzing the trace 290 as described above. FIG. 26 thus further supports the conclusion that the test system 220 of the present invention detects and identifies, from a remote location, corrosion on the conductive member 222.

The delay in the amount of time that it takes to polarize and depolarize the conductive member can also be used to detect areas of corrosion. As generally described above, the Applicants have discovered that the corroded sections polarize and depolarize at a different rate than clear pipe with no corrosion. FIG. 26 contains three traces 298a, 298b, and 298c representing data measured using the test system 220 to illustrate remote activation of a corrosion patch on steel pipe under three different bias conditions. These traces 298a, 298b, and 298c are compared in FIG. 26 to a trace 298d associated with a marker element 284 as depicted in FIG. 23A.

These traces 298a, 298b, and 298c illustrate detection of corrosion by subtraction of pairs of waveforms taken at different times. The trace 298a illustrates impedance change data measured after three minutes of negative polarity subtracted from impedance data associated with a baseline reference taken prior to negative polarization. Trace 298a shows a relatively severe increase in slope at the location of known corrosion anomalies as compared to a relatively flat slope prior to the location of the corrosion anomaly.

Trace 298b illustrates impedance change resulting from depolarization by subtracting measurements taken at three minutes of depolarization from the baseline reference measurements taken prior to depolarization. Trace 298a shows a decrease in slope after a slow increase in slope prior to the location of known corrosion anomalies.

Trace 298c illustrates impedance change resulting from positive polarization subtracting measurements taken after three minutes of positive polarization from a base line trace measurements taken prior to positive polarization. Trace 298c shows a slight decrease in slope after a relatively flat to increase in slope prior to the location of known corrosion anomalies.

The foregoing discussion illustrates that the signals generated by the exciting system 268 may be combined with signals generated by the perturbation system 270 in various ways to obtain data associated with anomalies in elongate conductive members.

What is claimed is:

1. A method of analyzing a conductive pipe member for the presence an anomaly the electromagnetic properties of which are non-linear, comprising the steps of:
    altering the electromagnetic properties of the pipe member at the anomaly by applying a perturbation signal to the pipe member, where the perturbation signal is at least one of a direct current signal and a pulsed signal;
    applying at least one test source signal to a first test location on the pipe member remote from the anomaly to cause the at least one test source signal to travel along the pipe through the anomaly;
    detecting at least one test return signal associated with the at least one test source signal traveling through the anomaly; and
    analyzing the at least one test return signal for characteristics associated with the anomaly.

2. A method as recited in claim 1, in which the pipe member is in an unperturbed state prior to the application of the perturbation signal, further comprising the steps of:
    when the pipe member is in the unperturbed state, applying at least one reference source signal to the first test location to cause the at least one reference source signal to travel along the pipe member through the anomaly;
    detecting at least one reference return signal associated with the at least one the reference source signal traveling through the anomaly; and
    analyzing the at least one reference return signal.

3. A method as recited in claim 2, in which the step of analyzing the at least one test return signal for characteristics associated with the anomaly comprises the step of comparing the at least one reference return signal with the at least one test return signal.

4. A method as recited in claim 1, in which the electromagnetic properties of the of the pipe member at the anomaly vary in a non-linear manner in response the at least one perturbation signal.

5. A method as recited in claim 1, in which the electromagnetic properties of the pipe member at the anomaly vary in a non-linear manner in response changes in the at least one perturbation signal.

6. A method as recited in claim 1, in which the electromagnetic properties of the pipe member at the anomaly altered by the at least one perturbation signal include at least one of resistance, inductance, and capacitance at the location of the anomaly.

7. A method as recited in claim 1, further comprising the step of measuring a length of time between application of a given test source signal to the pipe member and measurement of the at least one test return signal associated with the given test source signal.

8. A method as recited in claim 1, further comprising the step of detecting a decay time associated with depolarization of the pipe member in response to removal of the at least one perturbation signal.

9. A method as recited in claim 1, further comprising the step of altering the perturbation signal, wherein:
    the step of applying the at least one test source signal comprises the steps of
        applying a first test source signal, and
        applying a second test source signal, where
            the first test source signal is applied before the at least one perturbation signal is altered, and
            the second test source signal is applied after the at least one perturbation signal is altered;
    the step of detecting the at least one test return signal comprises the steps of
        detecting a first test return signal in response to the first test source signal, and
        detecting a second test return signal in response to the second test source signal; and
    analyzing the first and second test return signals for characteristics associated with the anomaly.

10. A method as recited in claim 9, in which the step of altering the perturbation signal comprises the step of reversing a polarity of the perturbation signal.

11. A method as recited in claim 10, in which the step of altering the perturbation signal comprises the step of altering at least one of a voltage level, current level, magnetic field, or electric field of the perturbation signal.

12. A method as recited in claim 1, in which the step of analyzing the at least one test return signal comprises the steps of:
    obtaining a plurality of data sets, where each data set is associated with one test return signal; and
    averaging the plurality of sets of data.

13. A method as recited in claim 1, in which the step of analyzing the at least one test return signal comprises the steps of:

obtaining a plurality of data sets, where each data set is associated with a perturbation condition associated with a perturbation signal; and processing the plurality of data sets.

14. A method as recited in claim 13, in which the step of processing the plurality of data sets comprises the step of subtracting one of the plurality of data sets from another of the plurality of data sets.

15. A method as recited in claim 1, further comprising the step of removing the at least one perturbation signal from the pipe member, in which:

the step of applying the test source signal comprises the steps of applying a first test source signal, and applying a second test source signal, where the first test source signal is applied before the at least one perturbation signal is removed, and the second test source signal is applied after the at least one perturbation signal is removed;

the step of detecting the at least one test return signal comprises the steps of detecting first and second test return signals in response to the first and second test source signals, respectively; and the step of analyzing the at least one test return signal comprises the step of analyzing the first and second test return signals for characteristics associated with the anomaly.

16. A method as recited in claim 1, further comprising the step of connecting a marker element between the pipe member at a known location.

17. A method as recited in claim 16, in which the step of analyzing the at least one test return signal comprises the step of calibrating for the environment surrounding the pipe member based on at least one test return signal associated with the marker element.

18. A method as recited in claim 16, in which the step of analyzing the at least one test return signal comprises the step of determining a location of the anomaly based on at least one test return signal associated with the marker element.

19. A method as recited in claim 1, in which the perturbation signal is a remotely injected current flowing along the pipe member that causes a magnetic field at the anomaly.

20. A method as recited in claims 19, in which the magnetic field causes a change in magnetic permeability of materials at the site of the anomaly.

21. A method as recited in claim 1, in which the perturbation signal is a magnetic field applied at the site of the anomaly.

22. A method as recited in claim 1, in which the perturbation signal causes a magnetic field at the anomaly that results in a change in magnetic permeability of materials at the anomaly.

23. A method as recited in claim 1, in which the perturbation signal is an imposed electric potential between the pipe member and an environment surrounding the pipe member that causes an electric field at the site of the anomaly.

24. A method as recited in claim 23, in which the electric field surrounds the pipe member to cause a change in resistivity of material at the site of the anomaly.

25. A method as recited in claim 23, in which the electric field causes a change in electric permittivity of material at the site of the anomaly.

26. A method as recited in claim 1, in which the perturbation signal results in an electric field surrounding the pipe member that causes a change in resistivity of material at the site of the anomaly.

27. A method as recited in claim 1, in which the perturbation signal results in an electric field surrounding the pipe member that causes a change in electric permittivity of material at the site of the anomaly.

28. A method as recited in claim 1, in which the perturbation signal results in an electric field surrounding the pipe member that causes a change in electric permittivity of material at the site of the anomaly.

29. A method as recited in claim 1, in which perturbation signal is switched on and off to control properties of material at the site of the anomaly.

30. A method as recited in claim 1, in which the perturbation signal is switched from off to on with a substantially step shaped waveform.

31. A method as recited in claim 1, in which the perturbation signal is pulsed with a waveform.

32. A method as recited in claim 1, in which:

a case member at least partly surrounds the pipe member; and at least one of the at least one source test signal and the at least one return test signal is propagated in a space between the pipe member and the case member.

33. A method as recited in claim 32, in which at least one of the at least one source test signal and the at least one return test signal is propagated as at least one of a transverse electromagnetic, transverse electric, and transverse magnetic electromagnetic wave.

34. A method as recited in claim 1, in which at least one of the at least one source test signal and the at least one return test signal is propagated as at least one of a transverse electromagnetic, transverse electric, and transverse magnetic electromagnetic wave.

* * * * *